United States Patent
Klinge et al.

(10) Patent No.: US 6,440,975 B1
(45) Date of Patent: *Aug. 27, 2002

(54) AMINO ACID DERIVATIVES, THE PREPARATION AND USE THEREOF AS ENDOTHELIN ANTAGONISTS

(75) Inventors: Dagmar Klinge, Heidelberg; Wilhelm Amberg, Friedrichsdorf; Andreas Kling, Mannheim; Hartmut Riechers, Neustadt; Liliane Unger, Ludwigshafen; Manfred Raschack, Weisenheim, all of (DE)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,020
(22) PCT Filed: Sep. 26, 1996
(86) PCT No.: PCT/EP96/04205
§ 371 (c)(1),
(2), (4) Date: Mar. 31, 1998
(87) PCT Pub. No.: WO97/12878
PCT Pub. Date: Apr. 10, 1997

(30) Foreign Application Priority Data

Oct. 4, 1995 (DE) .......................................... 195 36 891

(51) Int. Cl.$^7$ ................... C07D 239/42; A61K 31/505; A61P 9/12
(52) U.S. Cl. ................... 514/256; 514/269; 514/275; 544/323; 544/324; 544/326; 544/328; 544/330; 544/331; 544/332
(58) Field of Search ................ 544/323, 324, 544/326, 328, 330, 331, 332; 514/256, 269, 275

(56) References Cited

U.S. PATENT DOCUMENTS

| | | | |
|---|---|---|---|
| 4,092,150 A | * | 5/1978 | Treves .......................... 71/92 |
| 5,840,722 A | * | 11/1998 | Baumann et al. ........... 514/241 |
| 5,958,934 A | * | 9/1999 | Berger et al. ............... 544/331 |

FOREIGN PATENT DOCUMENTS

| | | |
|---|---|---|
| EP | 347 811 | 12/1989 |
| EP | 481 512 | 4/1992 |
| EP | 517 215 | 12/1992 |
| WO | WO 92/14715 | 9/1992 |
| WO | 95/26716 | * 10/1995 |
| WO | 96/11914 | * 4/1996 |

OTHER PUBLICATIONS

Database CAPLUS on STN, Chemical Abstract, vol. 83, No. 22276, Izergina et al., "Effect of some pyrimidine amino acid derivatives on vaccinia virus in tissue culture,"abstract, Vopr. Virusol., vol. 1, pp. 51–54, 1975.*

* cited by examiner

*Primary Examiner*—Richard L. Raymond
*Assistant Examiner*—Venkataraman Balasubramanian
(74) *Attorney, Agent, or Firm*—Keil & Weinkauf

(57) ABSTRACT

The invention relates to amino acid derivatives of the formula I

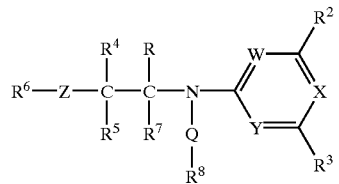

where the radicals have the meanings stated in the description, and to the use thereof as drugs.

23 Claims, No Drawings

AMINO ACID DERIVATIVES, THE PREPARATION AND USE THEREOF AS ENDOTHELIN ANTAGONISTS

The present invention relates to novel amino acid derivatives and to their preparation and use.

Endothelin is a peptide which is composed of 21 amino acids and which is synthesized and released by the vascular endothelium. Endothelin exists in three isoforms ET-1, ET-2 and ET-3. "Endothelin" or "ET" hereinafter means one or all endothelin isoforms. Endothelin is a potent vasoconstrictor and has a strong effect on vascular tone. It is known that this vasoconstriction is caused by binding of endothelin to its receptor (Nature 332 (1988) 411–415; FEBS Letters 231 (1988) 440–444, and Biochem. Biophys. Res. Commun. 154 (1988) 868–875).

Elevated or abnormal release of endothelin causes a persistent vasoconstriction in the peripheral, renal and cerebral blood vessels, which may lead to illnesses. As reported in the literature, elevated plasma endothelin levels are found in patients with hypertension, acute myocardial infarct, pulmonary hypertension, Raynaud's syndrome, atherosclerosis and in the airways of asthmatics (Japan J. Hypertension 12 (1989) 79, J. Vascular Med. Biology 2 (1990) 207, J. Am. Med. Association 264 (1990) 2868).

Accordingly, substances which specifically inhibit the binding of endothelin to the receptor ought also to antagonize the various abovementioned physiological effects of endothelin and therefore be valuable drugs.

We have found that certain amino acid derivatives are good inhibitors of endothelin receptors.

The invention relates to amino acid derivatives of the formula I

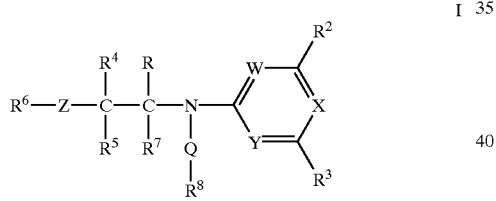

where R is formyl, tetrazolyl, cyano, COOH or a radical which can be hydrolyzed to COOH, for example R is

where $R^1$ has the following meanings:
a) hydrogen
b) succinimedyl
c) a 5-membered heteroaromatic ring which is linked via a nitrogen atom, such as pyrrolyl, pyrazolyl, imidazolyl and triazolyl, which can carry one or two halogen atoms or one or two $C_1$–$C_4$-alkyl or one or two $C_1$–$C_4$-alkoxy groups;
d) $R^1$ is furthermore

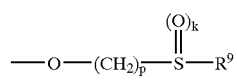

where k can assume the values 0, 1 and 2, p can assume the values 1, 2, 3 and 4, and $R^9$ is $C_1$–$C_4$-alkyl, $C_3$–$C_7$-cycloalkyl, $C_3$–$C_6$-alkenyl, $C_3$–$C_6$-alkynyl or unsubstituted or substituted phenyl which can be substituted by one or more, eg. from one to three, of the following radicals: halogen, nitro, cyano, $C_1$–$C_4$-alkyl, $C_1$–$C_4$-haloalkyl, hydroxyl, $C_1$–$C_4$-alkoxy, $C_1$–$C_4$-alkylthio, mercapto, amino, $C_1$–$C_4$-alkylamino, $C_1$–$C_4$-dialkylamino;

e) $R^1$ is furthermore $OR^{10}$ where $R^{10}$ is: hydrogen, the cation of an alkali metal such as lithium, sodium, potassium or the cation of an alkaline earth metal such as calcium, magnesium and barium, and physiologically tolerated alkylammonium ion or the ammonium ion, $C_3$–$C_8$-cycloalkyl such as cyclopropyl, cyclobutyl, cyclopentyl, cyclohexyl, cycloheptyl or cyclooctyl, $C_1$–$C_8$-alkyl, in particular $C_1$–$C_4$-alkyl such as methyl, ethyl, n-propyl, isopropyl, n-butyl, isobutyl, tert-butyl;

$CH_2$-phenyl which can be substituted by one or more of the following radicals: halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino, $C_1$–$C_4$-dialkylamino, $C_3$–$C_6$-alkenyl or $C_3$–$C_6$-alkynyl, it being possible for these groups in turn to carry from one to five halogen atoms;

$R^{10}$ can furthermore be a phenyl radical which can carry from one to five halogen atoms and/or from one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino, $C_1$–$C_4$-dialkylamino;

a 5-membered heteroaromatic ring which is linked via a nitrogen atom and contains from one to three nitrogen atoms and can carry one or two halogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio, in particular 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3,4-dichloro-1-imidazolyl;

f) $R^1$ is furthermore

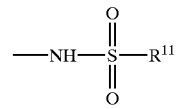

where $R^1$ is: $C_1$–$C_4$-alkyl, $C_3$–$C_6$-alkenyl, $C_3$–$C_6$-alkynyl, $C_3$–$C_8$-cycloalkyl as mentioned above in particular, it being possible for these radicals to carry a $C_1$–$C_4$-alkoxy, $C_1$–$C_4$-alkylthio and/or a phenyl radical as mentioned above;

phenyl which is unsubstituted or substituted, in particular as mentioned above;

g) $R^1$ is

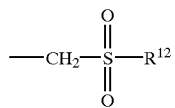

where $R^{12}$ has the same meaning as $R^{11}$;
h) $R^1$ can furthermore be

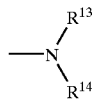

where $R^{13}$ and $R^{14}$ can be identical or different and have the following meanings:
hydrogen, $C_1$–$C_7$-alkyl, $C_3$–$C_7$-cycloalkyl, $C_3$–$C_7$-alkenyl, $C_3$–$C_7$-alkynyl, benzyl, phenyl, unsubstituted or substituted, as described above,
or $R^{13}$ and $R^{14}$ together form a $C_4$–$C_7$-alkylene chain which is closed to form a ring and is unsubstituted or substituted, eg. by $C_1$–$C_4$-alkyl, and which may contain a hetero atom, eg. oxygen, nitrogen or sulfur, such as —$(CH_2)_4$—, —$(CH_2)_5$—, —$(CH_2)_6$—, —$(CH_2)_7$—, —$(CH_2)_2$—O—$(CH_2)_2$—, —$(CH_2)_2$—S—$(CH_2)_2$—, —$CH_2$—NH—$(CH_2)_2$—, —$(CH_2)_2$—NH—$(CH_2)_2$—;
a tetrazole group or a nitrile group.
The other substituents have the following meanings:
W is nitrogen or C—$NO_2$, and W can furthermore be a CH group when one or more of the substituents $R^2$, $R^3$, $R^{15}$ and/or $R^{16}$ are nitro;
$R^2$ is hydrogen, halogen, $C_1$–$C_4$-alkyl, $C_1$–$C_4$-haloalkyl, $C_1$–$C_4$-alkoxy, $C_1$–$C_4$-haloalkoxy, hydroxyl, mercapto, $C_1$–$C_4$-alkylthio, nitro, amino, $C_1$–$C_4$-alkylamino or $C_1$–$C_4$-dialkylamino, cyano, phenyl, unsubstituted or mono- to trisubstituted by halogen, hydroxyl, amino, mono- or dialkyl-($C_1$–$C_3$)-amino, $C_1$–$C_3$-alkyl, $C_1$–$C_3$-alkoxy, mercapto or $C_1$–$C_3$-alkylthio; or a five- or six-membered heteroaromatic ring which contains from one to three nitrogen atoms and/or one sulfur or oxygen atom and which carries from one to three substituents as described above;
$R^2$ can furthermore form with the adjacent carbon atom and X a 5- or 6-membered alkylene or alkylidene ring in which, in each case, one or two carbon atoms can be replaced by a hetero atom such as nitrogen, sulfur or oxygen, and which can be mono- to trisubstituted by the following radicals: halogen, nitro, cyano, hydroxyl, mercapto, $C_1$–$C_3$-alkyl, $C_1$–$C_3$-haloalkyl, $C_1$–$C_3$-alkoxy, $C_1$–$C_3$-alkylthio, amino, $C_1$–$C_3$-alkylamino, $C_1$–$C_3$-dialkylamino;
X is nitrogen or $CR^{15}$ where $R^{15}$ is hydrogen or $C_1$–$C_5$-alkyl, $C_1$–$C_5$-alkoxy, $C_1$–$C_5$-alkylthio, nitro, phenyl, hydroxyl, mercapto, halogen, amino, $C_1$–$C_4$-alkylamino, $C_1$–$C_4$-dialkylamino or cyano,
or $CR^{15}$ is linked to $R^2$ to form a 5- or 6-membered ring as described above, and furthermore $CR^{15}$ can form together with $R^3$ and its adjacent carbon atom a 5- or 6-membered ring as described above;
$R^3$ can have the same meaning as $R^2$ and furthermore form together with the adjacent carbon atom and Y a 5- or 6-membered alkylene or alkylidene ring in which, in each case, one or two carbon atoms can be replaced by nitrogen, oxygen or sulfur; the 5- or 6-membered ring can be unsubstituted or mono- to trisubstituted by the following radicals; halogen, nitro, cyano, hydroxyl, mercapto, $C_1$–$C_3$-alkyl, $C_1$–$C_3$-haloalkyl, $C_1$–$C_3$-alkoxy, $C_1$–$C_3$-alkylthio, amino, $C_1$–$C_3$-alkylamino or $C_1$–$C_3$-dialkylamino; nitrogen in the 5-membered ring can also be substituted by a formyl or acetyl group; $R^2$ and $R^3$ can be identical or different;
Y is nitrogen or $CR^{16}$ where $R^{16}$ is hydrogen, $C_1$–$C_5$-alkyl, $C_1$–$C_5$-alkoxy, $C_1$–$C_5$-alkylthio, nitro, phenyl, hydroxyl, halogen, cyano, amino, $C_1$–$C_4$-alkylamino, $C_1$–$C_4$-dialkylamino or mercapto, or $CR^{16}$ forms together with $R^3$ and its adjacent carbon atom a 5- or 6-membered ring as described above;
$R^4$ is hydrogen, $C_1$–$C_7$-alkyl, $C_3$–$C_7$-cycloalkyl; or phenyl or naphthyl which can be substituted by one or more of the following radicals; halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, phenyl, $C_1$–$C_4$-alkylthio, amino, $C_1$–$C_4$-alkylamino or $C_1$–$C_4$-dialkylamino,
$R^4$ can also be a five- or six-membered heteroaromatic ring which contains one nitrogen, sulfur or oxygen atom and which can carry one or two of the following radicals: halogen, cyano, nitro, $C_1$–$C_4$-alkyl, $C_1$–$C_4$-haloalkyl, $C_1$–$C_4$-alkoxy, phenoxy, $C_1$–$C_4$-alkylthio, $C_1$–$C_4$-alkylamino or $C_1$–$C_4$-dialkylamino;
in addition, $R^4$ and $R^5$ can be phenyl groups which are connected to each other in the ortho positions by a direct linkage, a methylene, ethylene or ethenylene group, an oxygen or sulfur atom or an $SO_2$, NH or N-alkyl group;
$R^5$ is $C_1$–$C_7$-alkyl, $C_3$–$C_7$-cycloalkyl or phenyl or naphthyl which can be substituted by from one to three of the following radicals; halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, phenyl, $C_1$–$C_4$-alkylthio, amino, $C_1$–$C_4$-alkylamino or $C_1$–$C_4$-dialkylamino, where two radicals on adjacent carbon atoms can form together with the latter, connected via an alkylene or alkylidene group, a five- or six-membered ring in which one or more —$CH_2$— or —CH— groups can be replaced by oxygen, for example: —$(CH_2)_3$—, —$(CH_2)_4$—, —CH=CH—O—, —O—$CH_2$—O—, —O—$(CH_2)_2$—O—, —CH=CH—$CH_2$— or —O—CH=CH—O—;
$R^5$ can be, for example, the following radicals:

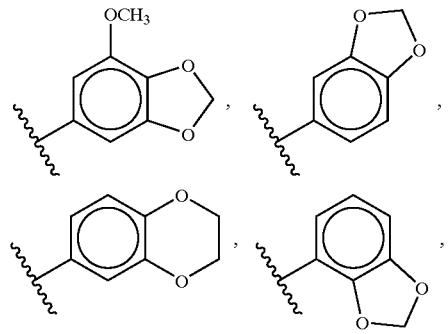

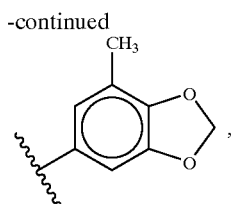

Furthermore, $R^5$ can be a five- or six-membered heteroaromatic ring which contains one nitrogen, sulfur or oxygen atom and which can carry one or two of the following radicals: halogen, cyano, nitro, $C_1$–$C_4$-alkyl, $C_1$–$C_4$-haloalkyl, $C_1$–$C_4$-alkoxy, phenoxy, $C_1$–$C_4$-alkylthio, $C_1$–$C_4$-alkylamino or $C_1$–$C_4$-dialkylamino; in addition, $R^5$ can form together with $R^4$ a tricyclic system as described above, and $R^5$ can additionally be an unsubstituted or substituted phenyl or heteroaromatic radical as described above which is linked in the ortho position to $R^8$ to form a 6-membered ring where Q must be a single bond and $R^8$ must be a CH-$R^{17}$ group;

$R^6$ is hydrogen, $C_1$–$C_4$-alkyl or $C_1$–$C_4$-haloalkyl

Z is a single bond, oxygen, sulfur, sulfoxide —SO— or sulfonyl;

$R^7$ is hydrogen or $C_1$–$C_4$-alkyl, $C_2$–$C_4$-alkylene, $C_2$–$C_4$-alkynyl;

Q is a single bond, a

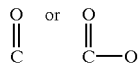

group $R^8$ is hydrogen, $C_1$–$C_4$-alkyl, $C_2$–$C_4$-alkylene, phenyl or benzyl, and $R^8$ can furthermore be directly connected to $R^5$ as described above, in which case $R^8$ is a CH—$R^{17}$ group where $R^{17}$ is hydrogen, $C_1$–$C_4$-alkyl, phenyl or phenyl which is mono- to trisubstituted by methoxy, or is one of the following radicals

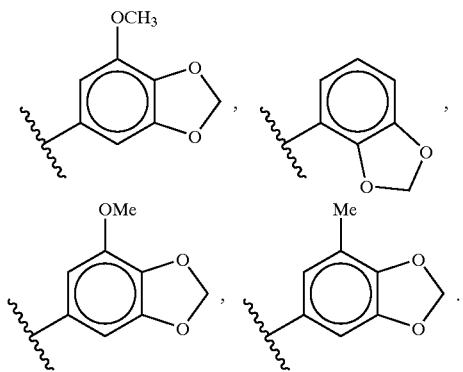

The compounds, as well as the intermediates II for preparing them, may have one or more asymmetrical substituted carbon atoms. Compounds of this type may exist as pure enantiomers or pure diastereomers or as mixture thereof. The use of an enantiomerically pure compound as active ingredient is preferred.

The invention furthermore relates to the use of the above-mentioned amino acid derivatives for producing drugs, in particular for producing inhibitors of endothelin receptors.

The compounds according to the invention are prepared by reacting an amino acid derivative II with a heterocyclic derivative III where $R^{17}$ is halogen or $R^{18}$—$SO_2$, where $R^{18}$ can be $C_1$–$C_4$-alkyl, $C_1$–$C_4$-haloalkyl or phenyl. In this, R is a carboxylic ester or a carboxylic acid. II with R=$CO_2$H is preferably used. If the preparation of II results in the amino acid ester, this is first hydrolyzed to the amino acid (R=$CO_2$H) by standard methods of amino acid chemistry.

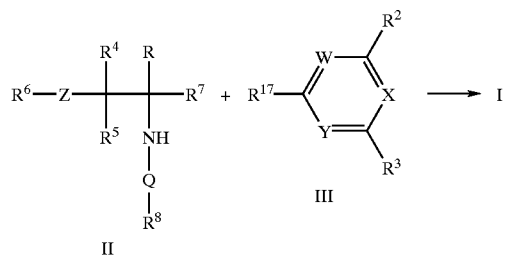

The reaction preferably takes place in an inert solvent with the addition of a base, as described in the literature, eg. in J. Am. Chem Soc. 98 (1976) 8472–8475 or J. Chem. Soc. Perkin Trans I (1988) 691–696.

Examples of such solvents or diluents are water, aliphatic, alicyclic and aromatic hydrocarbons, which may be chlorinated, such as hexane, cyclohexane, petroleum ether, naphtha, benzene, toluene, xylene, methylene chloride, chloroform, carbon tetrachloride, ethyl chloride and trichloroethylene, ethers such as diisopropyl ether, dibutyl ether, methyl tert-butyl ether, propylene oxide, dioxane and tetrahydrofuran, ketones such as acetone, methyl ethyl ketone, methyl isopropyl ketone and methyl isobutyl ketone, nitriles such as acetonitrile and propionitrile, alcohols such as methanol, ethanol, isopropanol, butanol and ethylene glycol, esters such as ethyl acetate and amyl acetate, amides such as dimethylformamide and dimethylacetamide, sulfoxides and sulfones such as dimethyl sulfoxide and sulfolane, bases such as pyridine, N-methylpyrrolidone, cyclic ureas such as 1,3-dimethyl-2-imidazolidinone and 1,3-dimethyl-3,4,5,6-tetrahydro-2(1H)-pyrimidinone.

The reaction is moreover preferably carried out at a temperature in the range from 0° C. to the boiling point of the solvent or mixture of solvents.

It is possible to use as base an alkali metal or alkaline earth metal hydride such as sodium hydride, potassium hydride or calcium hydride, a carbonate such as alkali metal carbonate, eg. sodium or potassium carbonate, an alkali metal or alkaline earth metal hydroxide such as sodium or potassium hydroxide, an organo-metallic compound such as butyllithium, or an alkali metal amide such as lithium diisopropylamide.

The invention also relates to those compounds of the formula II which have not been disclosed. They can be prepared in a known manner.

The compounds IIa according to the invention, where $R^6$=H and Z is a bond, can be prepared, for example, by a method described in Tetrahedron Lett. 30 (1978) 2651, by reacting a suitable imine IV with a compound V with the aid of a base in an inert solvent. This reaction is, where appropriate, carried out in a 2-phase mixture with a phase-transfer catalyst under phase-transfer conditions, for example in methylene chloride and 5–20% strength aqueous sodium hydroxide solution with a quaternary ammonium salt such as tetra-n-butylammonium bisulfate. In this, K means halogen or $OR^9$ where $R^{19}$ is methylsulfonyl, toluylsulfonyl or trifluoromethylsulfonyl. The imine VI is subsequently cleaved.

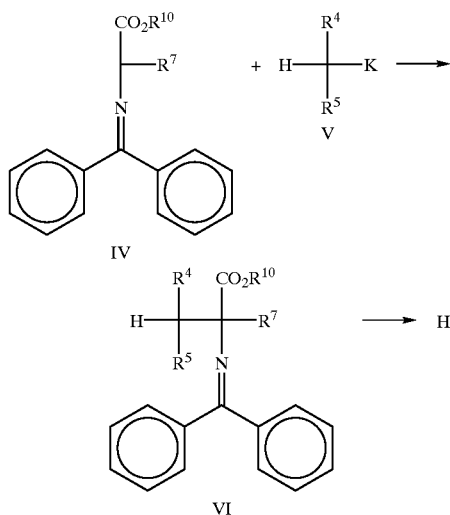

VI can be hydrolyzed to IIa in a suitable solvent using inorganic or organic strong acids such as hydrochloric acid, sulfuric acid, nitric acid, phosphoric acid, perchloric acid, acetic acid, trifluoromethylsulfonic acid or trifluoroacetic acid in various concentrations. Solvents which can be used are water, $C_1$–$C_4$-alcohols, acetonitrile, diethyl ether, tetrahydrofuran, dioxane or toluene. As a rule, the hydrolysis takes place in two stages. In the first step, VI is hydrolyzed with dilute acid to the amino acid ester IIa where $R^{10}\neq$hydrogen. Thereafter the amino acid ester is hydrolyzed with more concentrated acid or with a strong acid to the amino acid IIa where $R^{10}$=H.

Reaction of compound IIa with III as described above results in compounds Ia according to the invention where $R^6$ is hydrogen, $R^8$ is hydrogen and Z and Q are each a single bond.

The compounds IIb according to the invention where Z is a bond, $R^5$ is an aromatic or heteroaromatic radical and $R^6$ is a $C_1$–$C_4$-alkyl group are prepared by reacting a suitable phosphonate compound VII with a carbonyl compound VIII in a Wittig-Horner reaction to give the α,β-unsaturated compound IX

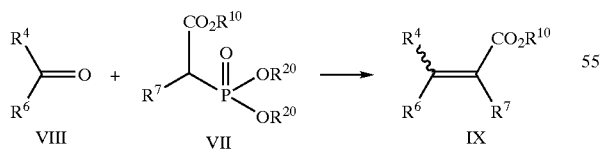

where $R^{20}$ is $C_1$–$C_6$-alkyl or benzyl.

Compound IX can be converted into the carboxylic acid derivative X by a method from Chem. Ber. 64 (1931) 1493 et seq. using $R^5$—H with the aid of a Friedel-Crafts catalyst such as aluminum trichloride.

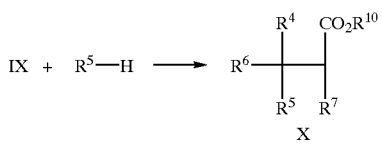

Compounds X can be converted by known methods into hydrazino acid derivatives XII as described, for example, in J. Am. Chem. Soc., 108 (1986) 6395–6397. The aminating reagent used is dialkyl azodicarboxylate XI where $R^{21}$ is 2,2-dimethylethyl or benzyl.

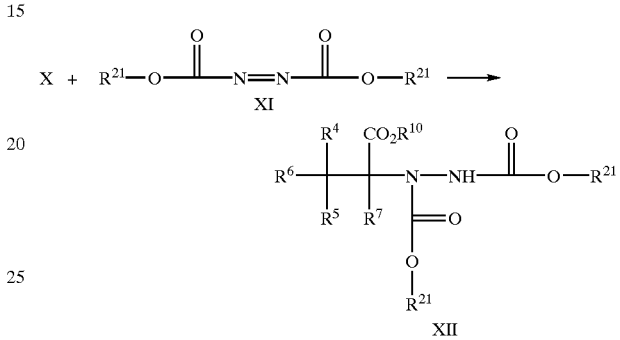

Hydrolysis of XII with a strong inorganic or organic acid in a suitable solvent as described above leads to the α-hydrazino carboxylic acid derivative XIII. If $R^{21}$ is benzyl, the conversion of XII into XIII can also take place by hydrogenolysis with hydrogen and a suitable catalyst such as palladium on active carbon of various concentrations, for example 10% palladium on carbon.

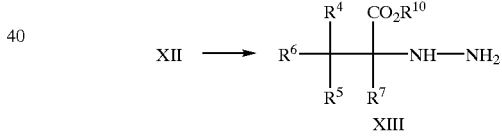

α-Hydrazino carboxylic acid derivatives XIII can be reduced with hydrogen under pressure, eg. 10–50 bar, with a suitable catalyst, eg. Raney nickel, to the α-amino acid derivatives IIb.

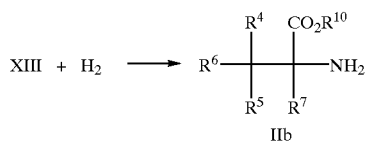

Compounds IIb can be reacted with III to give the compounds Ib according to the invention as described above.

Compounds IIb can also be prepared by reacting a compound XIV with a Grignard compound XV, and hydrolyzing the product XVI with acid to IIb, similar to the description in Liebigs Ann. (1977) 1174–1182:

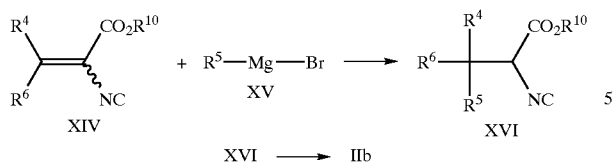

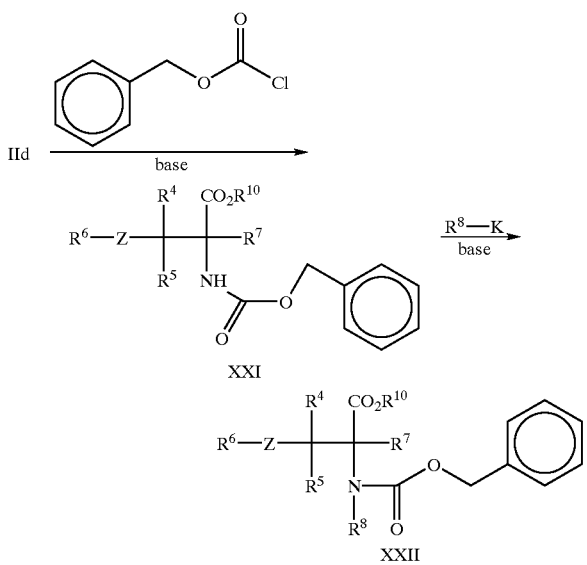

The compounds IIc according to the invention where $R^6$ is $C_1$–$C_4$-alkyl, and Z is oxygen, sulfur, S=O or $SO_2$, can be prepared by opening a suitable aziridine XVII with an alcohol or thiol $R^6$—Z—H to give XVIII.

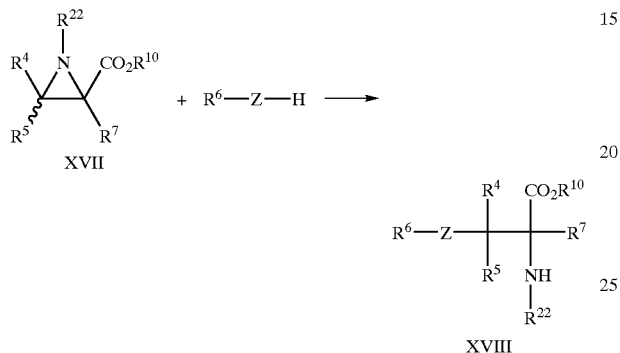

This method is described, for example, in J. Chem. Soc. Perkin Trans. II (1981) 121–126. Subsequent oxidation, eg. with metachloroperbenzoic acid in a suitable solvent, in the case where Z=sulfur provides the corresponding compounds XVIII with Z=SO or $SO_2$ depending on the molar ratio of the components. $R^{22}$ is hydrogen or a suitable protective group such as benzyl, benzyloxycarbonyl, tert-butyloxycarbonyl. If $R^{22}$ is hydrogen, then XVIII corresponds to IIc. When $R^{22}\ne$hydrogen, the protective group must be removed by known methods of hydrolysis, with addition of acid, or hydrogenolysis with a suitable catalyst to result in compound IIe in this way. The compounds IIc according to the invention can be reacted as described above with III to give Ic.

Compounds XVII, which are likewise according to the invention, can be prepared by reacting α,β-unsaturated carbonyl compounds XIX which are known or have been prepared by known methods with an aminating reagent XX and a suitable catalyst, for example as disclosed in J. Org. Chem. 56 (1991) 6744–6.

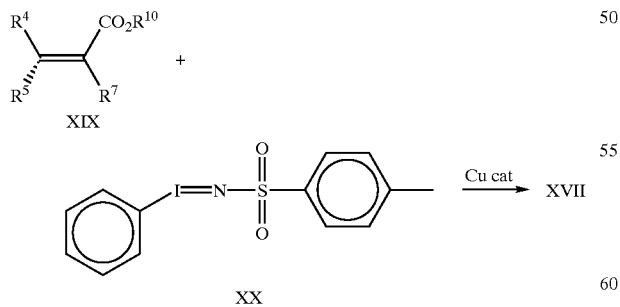

The compounds Id according to the invention where Q is a bond and $R^8$ is not hydrogen can be prepared by converting an amino acid derivative IId (Q is a bond and $R^8$ is hydrogen) by known methods for example into an N-benzyloxycarbonyl derivative XXI and reacting the latter in an inert solvent, eg. tetrahydrofuran, with a strong base, eg. potassium tert-butoxide, and an alkylating agent $R^8$—K where K is normally halogen or sulfate. The derivative XXII resulting from this can be deprotected by known methods to give the amino compound IIe, for example by eliminating the benzyloxycarbonyl group with hydrogen with catalysis by palladium/active carbon in an inert solvent.

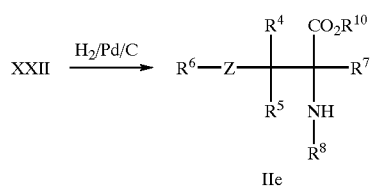

IIe is then reacted with III to give compounds Id as described above.

The compounds Ie according to the invention where Q is a

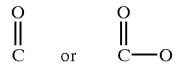

group can be prepared, for example, by reacting compounds Ia–d with XXIII under basic conditions in an inert solvent to give Ie.

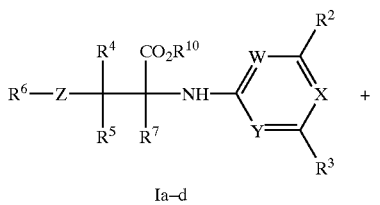

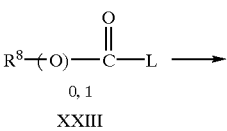

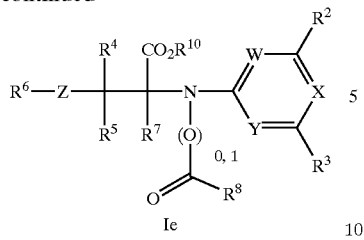

Ie

In this, L is halogen, $OR^{23}$ where $R^{23}$ is one of the following radicals: $C_1$–$C_4$-alkyl, benzyl, succinimidyl or 2,4,5-trichlorophenyl; L can also be azido, p-tolylsulfonyl, methylsulfonyl, trifluoromethylsulfonyl or an anhydride moiety.

The compounds If according to the invention where $R^5$ is linked to $R^8$ can be prepared from the tetrahydroisoquinoline derivatives IIf, which in turn can be prepared from the amino acid derivatives IId by reacting with aldehydes of the structure XXIV in the presence of acid, eg. hydrochloric acid or sulfuric acid, similar to Synthesis (1990) 550–556.

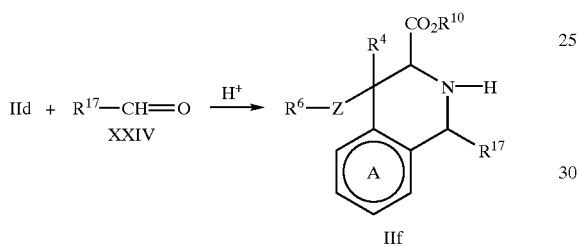

A $\stackrel{\frown}{=}$ aromatic or heteroaromatic system, unsubstituted or substituted IIf is then reacted with III to give compound If as described above.

Compounds of the formula I can be obtained in enantiomerically pure form by starting from enantiomerically pure compounds II which can be prepared in enantiomerically pure and, where appropriate, diastereomerically pure form by classical racemate resolution or by enantioselective syntheses (eg. Pure Appl. Chem. 55 (1983) 1799 et seq.; Helv. Chim. Acta 71 (1988) 224 et seq.; J. Am. Chem. Soc, 110 (1988) 1547–1557; Chem. Eng. News (1989) 25–27), and reacting these compounds II with III as described above. Another possibility for obtaining enantiomerically pure compounds of the formula I is classical racemate resolution of racemic or diastereomeric compounds I with suitable enantiomerically pure bases such as brucine, strychnine, quinine, quinidine, cinchonidine, cinchonine, yohimbine, morphine, dehydroabietylamine, ephedrine (−), (+), deoxyephedrine (+), (−), threo-2-amino-1-(p-nitrophenyl)-1,3-propanediol (+), (−), threo-2-(N,N-dimethylamino)-1-(p-nitrophenyl)-1,3-propanediol (+), (−) threo-2-amino-1-phenyl-1,3-propanediol (+), (−), α-methylbenzylamine (+), (−), α-(1-naphthyl)ethylamine (+), (−), α-(2-naphthyl)ethylamine (+), (−), aminomethylpinone, N,N-dimethyl-1-phenylethylamine, N-methyl-1-phenylethylamine, 4-nitrophenylethylamine, pseudoephedrine, norephedrine, norpseudoephedrine, amino acid derivatives and peptide derivatives.

Preferred compounds of the formula I, both as pure enantiomers and pure diastereomers or as mixture thereof, are those in which the substituents have the following meanings:

R is a carboxylic acid, a carboxylic acid salt or a group which can be hydrolyzed to a carboxylic acid, as described above.

$R^2$ is hydrogen, halogen, $C_1$–$C_4$-alkyl, $C_1$–$C_4$-haloalkyl, nitro, $C_1$–$C_4$-alkoxy, $C_1$–$C_5$-alkylthio, cyano, amino, methylamino, hydroxyl or dimethylamino;

W is nitrogen, C—$NO_2$, also CH when at least one of the radicals $R^2$, $R^3$, $R^{15}$ and $R^{16}$ is a nitro group;

X is nitrogen or $CR^{15}$ where $R^{15}$ is hydrogen, $C_1$–$C_4$-alkyl, $C_1$–$C_4$-alkoxy, nitro, cyano, halogen or phenyl, or $CR^{15}$ forms with $R^3$ and the adjacent carbon atom a 5- or 6-membered alkylene or alkylidene ring in which one or two carbon atoms can be replaced by a hetero atom such as nitrogen, oxygen or sulfur, and which can be mono- or disubstituted by a $C_1$–$C_3$-alkyl (or $C_1$–$C_3$-alkoxy group); nitrogen in a 5-membered ring may additionally be substituted by a CHO or $COCH_3$ group;

$R^3$ can have the same meaning as $R^2$ and additionally form with X and the adjacent carbon atom an unsubstituted or substituted 5- or 6-membered ring as described above; $R^3$ can furthermore form with the adjacent carbon atom and Y a 5- or 6-membered alkylene or alkylidene ring in which one or two carbon atoms can be replaced by nitrogen, oxygen or sulfur and which can be mono- or disubstituted by a $C_1$–$C_3$-alkyl or $C_1$–$C_3$-alkoxy group, and a nitrogen atom in a 5-membered ring can be substituted by a CHO or $COCH_3$ group;

$R^4$ has the meaning of hydrogen, $C_1$–$C_6$-alkyl, $C_3$–$C_7$-cycloalkyl or phenyl which can be substituted by one or more of the following radicals: halogen, $C_1$–$C_4$-alkyl, $C_1$–$C_4$-alkoxy, phenyl, furthermore $R^4$ and $R^5$ can be phenyl groups which are connected to each other in the ortho positions by a direct linkage, a $CH_2$ group, a $CH_2$—$CH_2$ group or an oxygen atom;

$R^5$ can have the same meaning as $R^4$ apart from hydrogen and $C_1$–$C_6$-alkyl, $R^5$ can additionally be phenyl which can be substituted exclusively or in addition to the abovementioned radicals by two radicals on adjacent carbon atoms, which together represent a 1,3-dioxomethylene or 1,4-dioxoethylene group and form with the adjacent carbon atoms a 5- or 6-membered ring;

$R^6$ is hydrogen or $C_1$–$C_4$-alkyl;

Z is a single bond, oxygen or sulfur;

$R^7$ is hydrogen or $C_1$–$C_4$-alkyl;

Q is single bond, a carbonyl group or an oxycarbonyl group;

$R^8$ is hydrogen or $C_1$–$C_4$-alkyl.

Particularly preferred compounds of the formula I, both as pure enantiomers or pure diastereomers or as mixture thereof, are those in which the substituents have the following meanings:

R is a carboxylic acid, a carboxylic acid salt or a group which can be hydrolyzed to a carboxylic acid, as described above;

$R^2$ is hydrogen, chlorine, methyl, ethyl, $CF_3$, nitro, methoxy, ethoxy, hydroxyl, methylthio, amino, N-methylamino or dimethylamino;

W is nitrogen;

X is nitrogen or $CR^{15}$ where $R^{15}$ is hydrogen, methyl, nitro or cyano, or $CR^{15}$ forms with $R^3$ and the adjacent carbon atom a 5- or 6-membered alkylene or alkylidene ring in which one carbon atom can be replaced by oxygen, and which can be substituted by a methyl or methoxy group; the 5- or 6-membered alkylene or alkylidene ring can have the following structures, for example:

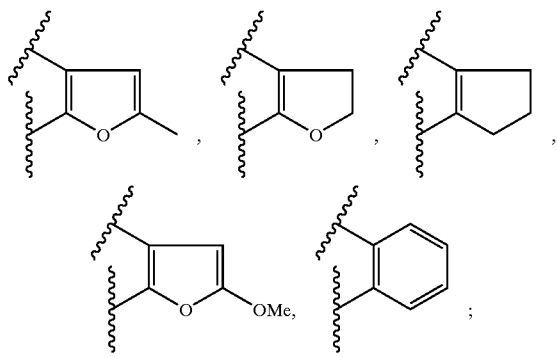

R³ can have the same meaning as R² and additionally form with X and the adjacent carbon atom an unsubstituted or substituted 5- or 6-membered ring as described above; R³ can furthermore form with the adjacent carbon atom a substituted or unsubstituted 5- or 6-membered alkylene or alkylidene ring in which one or two carbon atoms can be replaced by nitrogen or oxygen and which can be substituted by a methyl or methoxy group; examples of such alkylene or alkylidene rings are:

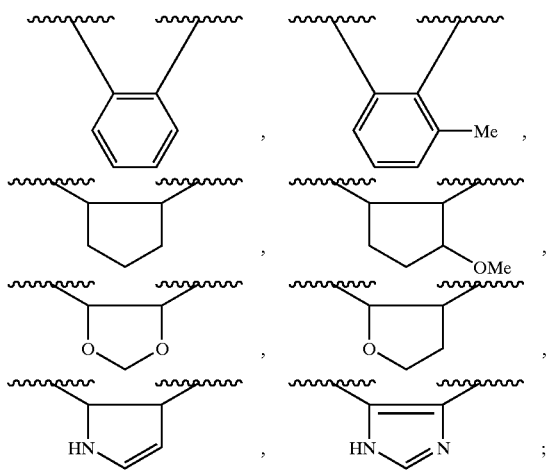

R⁴ has the meaning of hydrogen, methyl, ethyl, n-propyl, 1-methylethyl, cyclohexyl, or phenyl which can be substituted by one or two methoxy groups, furthermore R⁴ and R⁵ can be phenyl groups which are connected to each other in the ortho positions by a direct linkage, a CH₂ or CH₂–CH₂ group;

R⁵ is cyclohexyl or phenyl which can be substituted by phenyl, one to three methoxy groups, or exclusively or in addition to a methoxy group by two radicals on adjacent carbon atoms which together represent a 1,3-dioxomethylene or 1,4-dioxoethylene group and form with the adjacent carbon atoms a 5- or 6-membered ring, R⁵ can additionally be an unsubstituted or substituted phenyl ring which is linked in the ortho position to R⁸ to form a 6-membered ring when Q is a single bond and R⁸ is a CH—R¹⁷ group;

R⁶ is hydrogen, methyl, ethyl, n-propyl or 1-methylethyl;

R⁷ is hydrogen or methyl;

Q is a single bond, a carbonyl group or an oxycarbonyl group;

R⁸ is hydrogen, methyl or 1,1-dimethylethyl, R⁸ can additionally be directly connected to R⁵ as described above when R⁸ is a CH—R¹⁷ group in which R¹⁷ is hydrogen, methyl, ethyl, phenyl or phenyl which is mono- to trisubstituted by methoxy, or one of the following radicals:

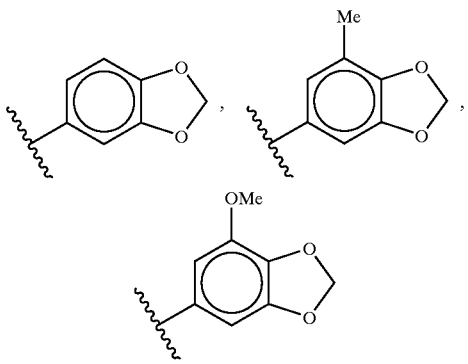

The compounds of the present invention provide a novel therapeutic potential for the treatment of hypertension, pulmonary hypertension, myocardial infarct, angina pectoris, acute kidney failure, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis following angioplasty, benign prostate hyperplasia, ischemic kidney failure and that caused by intoxication, and hypertension.

The good effect of the compounds can be shown in the following tests:

Receptor Binding Studies

Cloned human ETA receptor-expressing CHO cells and guinea-pig cerebellar membranes with >60% $ET_B$ by comparison with $ET_A$ receptors were used for the binding studies.

Membrane Preparation

The $ET_A$ receptor-expressing CHO cells were grown in $F_{12}$ medium containing 10% fetal calf serum, 1% glutamine, 100 U/ml penicillin and 0.2% streptomycin (Gibco BRL, Gaithersburg, Md., USA). After 48 h, the cells were washed with PBS and incubated with 0.05% trypsin-containing PBS for 5 min. The $F_{12}$ medium was then neutralized, and the cells were collected by centrifugation at 300×g. To lyse the cells, the pellet was briefly washed with lysis buffer (5 mM tris-HCl, pH 7.4 with 10% glycerol) and then incubated at a concentration of $10^7$ cells/ml of lysis buffer at 4° C. for 30 min. The membranes were centrifuged at 20,000×g for 10 min, and the pellet was stored in liquid nitrogen.

Guinea-pig cerebella were homogenized in a Potter-Elvejhem homogenizer and obtained by differential centrifugation at 1,000×g for 10 min and repeated centrifugation of the supernatant at 20,000×g for 10 min.

Binding Assays

For the $ET_A$ and $ET_B$, receptor binding assays, the membranes were suspended in incubation buffer (50 mM tris-HCl, pH 7.4 with 5 mM MnCl₂, 40 μg/ml bacitracine and 0.2% BSA) at a concentration of 50 μg of protein per assay mixture, and incubated with 25 pM $^{125}$I-ET₁, ($ET_A$ receptor assay) or 25 pM $^{125}$I-RZ₃ ($ET_B$ receptor assay) at 25° C. in the presence and absence of test substance. The non-specific binding was determined using $10^{-7}$ M $ET_1$. After 30 min, the free and bound radioligand were separated by filtration through GF/B glass fiber filters (Whatman, England) on a Skatron cell collector (Skatron, Lier, Norway), and the filters were washed with ice-cold tris-HCl buffer, pH 7.4 with 0.2% BSA. The radioactivity collected on the filters was quantified using a Packard 2200 CA liquid scintillation counter.

Functional in vitro assay system for searching for endothelin receptor (subtype A) antagonists This assay system is a functional, cell-based assay for endothelin receptors. When certain cells are stimulated with endothelin 1 (ET1) they show an increase in the intracellular calcium concentration. This increase can be measured in intact cells loaded with calcium-sensitive dyes.

Fibroblasts which had been isolated from rats and in which an endogenous endothelin receptor of subtype A had been detected were loaded with the fluorescent dye Fura 2-an as follows: After trypsinization, the cells were resuspended in buffer A (120 mM NaCl, 5 mM KCl, 1.5 mM $MgCl_2$, 1 mM $CaCl_2$, 25 mM HEPES, 10 mM glucose, pH 7.4). to a density of $2\times10^6$/ml and incubated with Fura 2-am (2 $\mu$M), Pluronic F-127 (0.04%) and DMSO (0.2%) at 37° C. in the dark for 30 min. The cells were then washed twice with buffer A and resuspended at $2\times10^6$/ml.

The fluorescence signal from $2\times10^5$ cells per ml with Ex/Em 380/510 was recorded continuously at 30° C. To the cells were added the test substances and after an incubation time of 3 min ET1. The maximum change in fluorescence was determined over 30 minutes. The response of the cells to ET1 without previous addition of a test substance served as control and was set equal to 100%.

In vivo Testing of ET Antagonists

Male SD rats weighing 250–300 g were anesthetized with amobarbital, artifically ventilated, vagotomized and pithed. The carotid artery and jugular vein were cathetized.

Intravenous administration of 1 $\mu$g/kg ET1 to control animals leads to a marked rise in blood pressure which persists for a lengthy period.

The test compounds were injected i.v. (1 ml/kg) into the test animals 5 min before ET1 administration. To determine the ET-antagonistic properties, the rise in blood pressure in the test animals was compared with that in the control animals.

Sudden Death of Mice Induced by Endothelin-1

The principle of the test is the inhibition of the sudden heart death of mice caused by endothelin, probably owing to constriction of the coronary vessels, by pretreatment with endothelin receptor antagonists. Intravenous injection of 10 nmol/kg endothelin in a volume of 5 ml/kg of body weight is followed within a few minutes by the death of the animals.

The lethal dose of endothelin-1 is checked in each case on a small group of animals. Intravenous administration of the test substance is usually followed after 5 min by the injection of endothelin-1 which was lethal in the reference group. The times before administration increase with other modes of administration, possibly up to several hours.

The survival rate is recorded, and effective doses which protect 50% of the animals from endothelin-induced heart death for 24 h or longer (ED 50) are determined.

Functional Test on Vessels for Endothelin Receptor Antagonists

First a contraction is induced by $K^+$ in segments of rabbit aorta after a previous tension of 2 g and a relaxation time of 1 h in Krebs-Henseleit solution at 37° C. and pH 7.3–7.4. Washing out is followed by construction of an endothelin dose-effect plot up to the maximum.

Potential endothelin antagonists are administered to other preparations of the same vessel 15 min before starting the endothelin dose-effect plot. The effects of endothelin are calculated as a % of the $K^+$-induced contraction. Effective endothelin antagonists result in a shift in the endothelin dose-effect plot to the right.

The compounds according to the invention can be administered orally or parenterally (subcutaneously, intravenously, intramuscularly, intraperitoneally) in a conventional way. Administration can also take place with vapors or sprays through the nasopharyngeal space.

The dosage depends on the age, condition and weight of the patient and on the mode of administration. As a rule, the daily dose of active ingredient is about 0.5–50 mg/kg of body weight on oral administration and about 0.1–10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. For this purpose the active ingredients can be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellent gases (cf. H. Sucker et al.: Pharmazeutische Technologie, Thieme-Verlag, Stuttgart, 1991). The administration forms obtained in this way normally contain from 0.1 to 90% by weight of active ingredient.

SYNTHESIS EXAMPLES

Example 1

Di(3-methoxyphenyl)methyl bromide 22.53 g (92.9 mmol) of di(m-methoxyphenyl)methyl alcohol were dissolved in 200 ml of diethyl ether and, under a nitrogen atmosphere, 28.76 g (138.3 mmol) of thionyl bromide dissolved in 20 ml of diethyl ether were added dropwise. After 6 hours at room temperature, the mixture was poured into ice-water, and the organic phase was separated off, washed with water and saturated $NaHCO_3$ solution, then dried with $MgSO_4$ and concentrated. 27.73 g (97.8%) of crude product were obtained and were immediately reacted further.

Example 2

Methyl 2-N-(diphenylmethylene)amino-3,3-di(3-methoxyphenyl)propionate 19.05 g (75.2 mmol) of N-diphenylmethylenylglycine methyl ester were dissolved in 200 ml of THF and, at −78° C. under an argon atmosphere, 75 ml of a 1.5 molar solution of LDA in THF were slowly added dropwise. After 45 minutes, 27.73 g (90.3 mmol) of di(3-methoxyphenyl) methyl bromide in 60 ml of THF were added dropwise. After 90 minutes, the mixture was allowed to reach room temperature and was then stirred for 22 hours. Then 20 ml of phosphate buffer were added, the THF was stripped off under reduced pressure, and the residue was extracted three times with ethyl acetate. The combined organic phases were dried with $MgSO_4$ and concentrated. 43.3 g of crude product were obtained and were immediately reacted further.

Example 3

Methyl 2-amino-3,3-di(3-methoxyphenyl)propionate 43.3 g (75.2 mmol) of methyl 2-N-(diphenylmethylene) amino-3,3-di(3-methoxyphenyl)propionate (crude product)

were dissolved in 1 l of THF and, after addition of 506 ml of 0.5 normal hydrochloric acid, stirred at room temperature for 90 minutes. After the THF had been stripped off under reduced pressure, the aqueous residue was extracted with ethyl acetate. The aqueous phase was then made alkaline (pH 9–10) with 25% strength ammonia solution.

The aqueous phase was then extracted four times with ethyl acetate. The combined organic phases were dried with $MgSO_4$ and concentrated. 14.27 g (60.1%) of product were obtained.

Example 4

2-Amino-3,3-di(3-methoxyphenyl)propionic acid 6.0 g (19.0 mmol) of methyl 2-amino-3,3-di(3-methoxyphenyl)propionate were refluxed in 140 ml of 6 normal hydrochloric acid for 6 hours. The mixture was then cooled to 0° C., and the precipitate was filtered off, washed with water and dried. The solid was then dissolved in 50 ml of ethanol, 20 ml of propene oxide were added and the mixture was refluxed for 30 minutes. After cooling, the precipitate was filtered off, washed with ethanol and dried. 2.20 g (38.4%) of a white powder of melting piont 168–173° C. were obtained.

Example 5

3,3-Di(3-methoxyphenyl)-2-(4,6-dimethoxy-2-pyrimidinylamino)-propionic acid 2.20 g (7.3 mmol) of 2-amino-3,3-di(3-methoxyphenyl) propionic acid, 0.66 g (3.04 mmol) of 4,6-dimethoxy-2-methylsulfonylpyrimidine and 0.39 g (3.65 mmol) of sodium carbonate were introduced into a mixture of 16 ml of DMF and 16 ml of water and stirred at 80° C. for 10 hours. Water and ethyl acetate were then added to the reaction mixture. The aqueous phase was acidified with 6 normal hydrochloric acid and extracted three times with ethyl acetate. Drying with $MgSO_4$ and concentration resulted in the crude product, which was chromatographed on silica gel with dichloromethane/methanol (50:1). 0.455 g (34.1%) of a white powder of melting point 58–66° C. was obtained.

Example 6

3,3-Diphenyl-2-(4,6-dimethyl-2-pyrimidinylamino) propionic acid 2.60 g (10.8 mmol) of 2-amino-3,3-diphenylpropionic acid and 0.64 g (4.5 mmol) of 2-chloro-4,6-dimethylpyrimidine were introduced into a mixture of 16 ml of DMF and 16 ml of water, 0.57 g (5.4 mmol) of sodium carbonate was added and the mixture was stirred at 80° C. for 24 hours. Then 100 ml of ethyl acetate and a little water were added, and the phases were separated. The aqueous phase was acidified (pH 1–2) with 6 normal hydrochloric acid. The resulting precipitate was filtered off with suction and washed with ethyl acetate, then dried. 0.30 g (19.2%) of a white powder of melting point 172–174° C. was obtained.

Example 7

2-(4,6-Dimethoxy-2-triazinylamino)-2-(9-fluorenyl) acetic acid 2.29 g (9.6 mmol) of 2-amino-2-(9-fluorenyl)acetic acid, 0.70 g (4.0 mmol) of 4,6-dimethoxy-2-chlorotriazine and 0.51 g (4.8 mmol) of sodium carbonate were introduced into a mixture of 16 ml of DMF and 16 ml of water and stirred at 80° C. for 13 hours. Then ethyl acetate and water were added and the phases were separated. The aqueous phase was acidified with 6 normal HCl and extracted three times with ethyl acetate. The organic phases were dried with $MgSO_4$ and concentrated. The crude product was chromatographed on silica gel with ethyl acetate/n-heptane (1:1). 0.44 g (29.1%) of a white powder was obtained; $R_F$=0.135, melting point 182–186° C.

Example 8

2-(3-Nitro-6-methoxy-2-pyridinylamino)-3,3-diphenylpropionic acid 2.50 g (10.4 mmol) of 2-amino-3,3-diphenylpropionic acid, 0.84 g (4.3 mmol) of 2-chloro-3-nitro-6-methoxypyridine and 0.55 g (5.2 mmol) of sodium carbonate were introduced into 18 ml of DMF and 18 ml of water, and the mixture was stirred at 80° C. for 5 hours. Ethyl acetate and water were then added, and the phases were separated. The aqueous phase was acidified with 6 normal hydrochloric acid and extracted three times with ethyl acetate. After drying with $MgSO_4$ and concentration under reduced pressure, the crude product was recrystallized from isopropanol. 0.34 g (20.1%) of a yellow powder of melting point 172–180° C. was obtained.

The examples listed in following Tables 1–5 can be prepared by the methods described at the outset.

TABLE 1

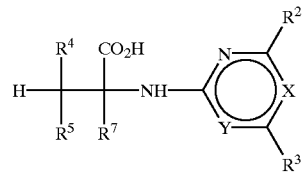

(I)

| No. | $R^4$ | $R^5$ | $R^7$ | $R^2$ | X | $R^3$ | Y | M.p. [° C.] |
|---|---|---|---|---|---|---|---|---|
| I-1 | H | Phenyl | H | Me | CH | Me | N | |
| I-2 | H | Phenyl | H | OMe | CH | Me | N | |
| I-3 | H | Phenyl | H | Me | CH | Me | N | |

TABLE 1-continued (I)

$$\text{H}-\underset{R^5}{\overset{R^4}{\text{C}}}-\underset{R^7}{\overset{CO_2H}{\text{C}}}-\text{NH}-\underset{Y}{\overset{N}{\bigcirc}}\underset{R^3}{\overset{R^2}{X}}$$

| No. | $R^4$ | $R^5$ | $R^7$ | $R^2$ | X | $R^3$ | Y | M.p. [° C.] |
|---|---|---|---|---|---|---|---|---|
| I-4 | H | Phenyl | H | Me | CH | Et | N | |
| I-5 | H | Phenyl | H | Et | CH | Et | N | |
| I-6 | H | Phenyl | H | $CF_3$ | CH | Me | N | |
| I-7 | H | Phenyl | H | $CF_3$ | CH | OMe | N | |
| I-8 | H | Phenyl | H | Me | C—$(CH_2)_3$ | — | N | |
| I-9 | H | Phenyl | H | OMe | C—$(CH_2)_3$ | — | N | |
| I-10 | H | Phenyl | H | OMe | C—$(CH_2)_2$ | O | N | |
| I-11 | H | Phenyl | H | OMe | N | OMe | N | |
| I-12 | H | Phenyl | H | OMe | N | Me | N | |
| I-13 | H | Phenyl | H | OMe | N | OMe | N | |
| I-14 | H | Phenyl | Me | OMe | CH | OMe | CH | |
| I-15 | H | Phenyl | Me | OMe | CH | Me | CH | |
| I-16 | H | Phenyl | Me | OMe | CH | N=C | N | |
| I-17 | H | Phenyl | H | OMe | N | H | —NH—C | |
| I-18 | H | Phenyl | H | OMe | N | H | C—$NO_2$ | |
| I-19 | H | Phenyl | H | OMe | C—Me | OMe | N | |
| I-20 | H | Phenyl | H | OMe | CH | Me | N | 188–193 |
| I-21 | H | Phenyl | H | H | N | $NH_2$ | CH | |
| I-22 | H | Phenyl | H | H | N | H | N | |
| I-23 | H | Phenyl | H | H | CH | OMe | N | |
| I-24 | Me | Phenyl | H | OMe | CH | OMe | N | |
| I-25 | Me | Phenyl | H | OMe | CH | Me | N | |
| I-26 | Me | Phenyl | H | Me | CH | Me | N | |
| I-27 | Me | Phenyl | H | Me | CH | Et | N | |
| I-28 | Me | Phenyl | H | Et | CH | Et | N | |
| I-29 | Me | Phenyl | H | Me | CH | $CF_3$ | N | |
| I-30 | Me | Phenyl | H | OMe | CH | $CF_3$ | N | |
| I-31 | Me | Phenyl | H | Me | C—$(CH_2)_3$— | | N | |
| I-32 | Me | Phenyl | H | OMe | C—$(CH_2)_3$— | | N | |
| I-33 | Me | Phenyl | H | OMe | C—$(CH_2)_3$—O | | N | |
| I-34 | Me | Phenyl | H | Me | C—$(CH_2)_3$—O | | N | |
| I-35 | Me | Phenyl | H | OMe | N | OMe | N | |
| I-36 | Me | Phenyl | H | OMe | CH | H | N | |
| I-37 | Me | Phenyl | H | OMe | N | OMe | CH | |
| I-38 | Me | Phenyl | H | Cl | N | Me | CH | |
| I-39 | Me | Phenyl | H | Me | N | Me | CH | |
| I-40 | Me | Phenyl | H | OMe | N | N=CH—NH—C | | |
| I-41 | Me | Phenyl | H | Cl | N | N=CH—NH—C | | |
| I-42 | Me | Phenyl | H | OMe | N | H | C—$NO_2$ | |
| I-43 | Me | Phenyl | H | OMe | C—Me | H | N | |
| I-44 | Me | Phenyl | H | Me | C—Me | H | N | |
| I-45 | Me | Phenyl | H | $NH_2$ | N | $NH_2$ | N | |
| I-46 | Me | Phenyl | H | $NHCH_3$ | N | $NHCH_3$ | N | |
| I-47 | Me | Phenyl | H | SMe | CH | H | N | |
| I-48 | Me | Phenyl | Me | OMe | CH | OMe | N | |
| I-49 | Me | Phenyl | Me | OMe | CH | Me | N | |
| I-50 | Me | Phenyl | Me | Me | CH | Me | N | |
| I-51 | Et | Phenyl | H | OMe | CH | OMe | N | |
| I-52 | Et | Phenyl | H | OMe | CH | Me | N | |
| I-53 | Et | Phenyl | H | Me | CH | Me | N | |
| I-54 | Et | Phenyl | H | Me | CH | Et | N | |
| I-55 | Et | Phenyl | H | Et | CH | Et | N | |
| I-56 | Et | Phenyl | H | Me | CH | $CF_3$ | N | |
| I-57 | Et | Phenyl | H | OMe | CH | $CF_3$ | N | |
| I-58 | Et | Phenyl | H | OMe | CH | H | N | |
| I-59 | Et | Phenyl | H | SMe | CH | H | N | |
| I-60 | Et | Phenyl | H | Et | CH | OMe | N | |
| I-61 | Et | Phenyl | H | Me | C—$(CH_2)_3$— | | N | |
| I-62 | Et | Phenyl | H | OMe | C—$(CH_2)_3$— | | N | |
| I-63 | Et | Phenyl | H | Me | C—$(CH_2)_2$—O | | N | |
| I-64 | Et | Phenyl | H | OMe | C—$(CH_2)_2$—O | | N | |
| I-65 | Et | Phenyl | H | OMe | N | OMe | N | |
| I-66 | Et | Phenyl | H | $NH_2$ | N | $NH_2$ | N | |
| I-67 | Et | Phenyl | H | NHMe | N | NHMe | N | |
| I-68 | Et | Phenyl | H | OMe | N | OMe | CH | |
| I-69 | Et | Phenyl | H | Me | N | Me | CH | |

TABLE 1-continued

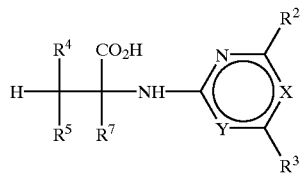

(I)

| No. | R⁴ | R⁵ | R⁷ | R² | X | R³ | Y | M.p. [° C.] |
|---|---|---|---|---|---|---|---|---|
| I-70 | Et | Phenyl | H | Cl | N | Me | CH | |
| I-71 | Et | Phenyl | H | OMe | N | N=CH—NH—C | | |
| I-72 | Et | Phenyl | H | Cl | N | N=CH—NH—C | | |
| I-73 | Et | Phenyl | H | OMe | N | H | C—NO₂ | |
| I-74 | Et | Phenyl | H | OMe | C—Me | H | N | |
| I-75 | Et | Phenyl | H | Me | C—Me | H | N | |
| I-76 | Et | Phenyl | Me | OMe | CH | OMe | N | |
| I-77 | Et | Phenyl | Me | OMe | CH | Me | N | |
| I-78 | Et | Phenyl | Me | Me | CH | Me | N | |
| I-79 | H | 4-Methoxyphenyl | H | OMe | CH | OMe | N | |
| I-80 | H | 4-Methoxyphenyl | H | OMe | CH | Me | N | |
| I-81 | H | 4-Methoxyphenyl | H | Me | CH | Me | N | |
| I-82 | H | 4-Methoxyphenyl | H | Me | CH | Et | N | |
| I-83 | H | 4-Methoxyphenyl | H | Et | CH | Et | N | |
| I-84 | H | 4-Methoxyphenyl | H | Me | CH | CF₃ | N | |
| I-85 | H | 4-Methoxyphenyl | H | OMe | CH | CF₃ | N | |
| I-86 | H | 4-Methoxyphenyl | H | OMe | CH | H | N | |
| I-87 | H | 4-Methoxyphenyl | H | SMe | CH | H | N | |
| I-88 | H | 4-Methoxyphenyl | H | Et | CH | OMe | N | |
| I-89 | H | 4-Methoxyphenyl | H | Me | C—(CH₂)₃— | | N | |
| I-90 | H | 4-Methoxyphenyl | H | OMe | C—(CH₂)₃— | | N | |
| I-91 | H | 4-Methoxyphenyl | H | Me | C—(CH₂)₂—O | | N | |
| I-92 | H | 4-Methoxyphenyl | H | OMe | C—(CH₂)₂—O | | N | |
| I-93 | H | 4-Methoxyphenyl | H | OMe | N | OMe | N | |
| I-94 | H | 4-Methoxyphenyl | H | NH₂ | N | NH₂ | N | |
| I-95 | H | 4-Methoxyphenyl | H | NHMe | N | NHMe | N | |
| I-96 | H | 4-Methoxyphenyl | H | OMe | N | OMe | CH | |
| I-97 | H | 4-Methoxyphenyl | H | Cl | N | Me | CH | |
| I-98 | H | 4-Methoxyphenyl | H | OMe | N | N=CH—NH—C | | |
| I-99 | H | 4-Methoxyphenyl | H | Cl | N | N=CH—NH—C | | |
| I-100 | H | 4-Methoxyphenyl | H | Me | N | Me | CH | |
| I-101 | H | 4-Methoxyphenyl | H | OMe | N | Me | CH | |
| I-102 | H | 4-Methoxyphenyl | H | OMe | N | H | C—NO₂ | |
| I-103 | H | 4-Methoxyphenyl | H | OMe | C—Me | H | N | |
| I-104 | H | 4-Methoxyphenyl | H | Me | C—Me | H | N | |
| I-105 | H | 4-Methoxyphenyl | Me | OMe | CH | OMe | N | |
| I-106 | H | 4-Methoxyphenyl | Me | OMe | CH | Me | N | |
| I-107 | H | 4-Methoxyphenyl | Me | Me | CH | Me | N | |
| I-108 | H | 3-Methoxyphenyl | H | OMe | CH | OMe | N | |
| I-109 | H | 3-Methoxyphenyl | H | OMe | CH | Me | N | |
| I-110 | H | 3-Methoxyphenyl | H | Me | CH | Me | N | |
| I-111 | H | 3-Methoxyphenyl | H | Me | CH | Et | N | |
| I-112 | H | 3-Methoxyphenyl | H | Et | CH | Et | N | |
| I-113 | H | 3-Methoxyphenyl | H | Me | CH | CF₃ | N | |
| I-114 | H | 3-Methoxyphenyl | H | OMe | CH | CF₃ | N | |
| I-115 | H | 3-Methoxyphenyl | H | OMe | CH | H | N | |
| I-116 | H | 3-Methoxyphenyl | H | SMe | CH | H | N | |
| I-117 | H | 3-Methoxyphenyl | H | Et | CH | OMe | N | |
| I-118 | H | 3-Methoxyphenyl | H | Me | C—(CH₂)₃— | | N | |
| I-119 | H | 3-Methoxyphenyl | H | OMe | C—(CH₂)₃— | | N | |
| I-120 | H | 3-Methoxyphenyl | H | Me | C—(CH₂)₂—O | | N | |
| I-121 | H | 3-Methoxyphenyl | H | OMe | C—(CH₂)₂—O | | N | |
| I-122 | H | 3-Methoxyphenyl | H | OMe | N | OMe | N | |
| I-123 | H | 3-Methoxyphenyl | H | NH₂ | N | NH₂ | N | |
| I-124 | H | 3-Methoxyphenyl | H | NHMe | N | NHMe | N | |
| I-125 | H | 3-Methoxyphenyl | H | OMe | N | OMe | CH | |
| I-126 | H | 3-Methoxyphenyl | H | Cl | N | Me | CH | |
| I-127 | H | 3-Methoxyphenyl | H | OMe | N | N=CH—NH—C | | |
| I-128 | H | 3-Methoxyphenyl | H | Cl | N | N=CH—NH—C | | |
| I-129 | H | 3-Methoxyphenyl | H | Me | N | Me | CH | |
| I-130 | H | 3-Methoxyphenyl | H | OMe | N | Me | CH | |
| I-131 | H | 3-Methoxyphenyl | H | OMe | N | H | C—NO₂ | |
| I-132 | H | 3-Methoxyphenyl | H | OMe | C—Me | H | N | |
| I-133 | H | 3-Methoxyphenyl | H | Me | C—Me | H | N | |
| I-134 | H | 3-Methoxyphenyl | Me | OMe | CH | OMe | N | |
| I-135 | H | 3-Methoxyphenyl | Me | OMe | CH | Me | N | |

TABLE 1-continued (I)

| No. | R⁴ | R⁵ | R⁷ | R² | X | R³ | Y | M.p. [° C.] |
|---|---|---|---|---|---|---|---|---|
| I-136 | H | 3-Methoxyphenyl | Me | Me | CH | Me | N | |
| I-137 | H | 3,4-Dimethoxyphenyl | H | OMe | CH | OMe | N | |
| I-138 | H | 3,4-Dimethoxyphenyl | H | OMe | CH | Me | N | |
| I-139 | H | 3,4-Dimethoxyphenyl | H | Me | CH | Me | N | |
| I-140 | H | 3,4-Dimethoxyphenyl | H | Me | CH | Et | N | |
| I-141 | H | 3,4-Dimethoxyphenyl | H | Et | CH | Et | N | |
| I-142 | H | 3,4-Dimethoxyphenyl | H | Me | CH | CF₃ | N | |
| I-143 | H | 3,4-Dimethoxyphenyl | H | OMe | CH | CF₃ | N | |
| I-144 | H | 3,4-Dimethoxyphenyl | H | OMe | CH | H | N | |
| I-145 | H | 3,4-Dimethoxyphenyl | H | SMe | CH | H | N | |
| I-146 | H | 3,4-Dimethoxyphenyl | H | Et | CH | OMe | N | |
| I-147 | H | 3,4-Dimethoxyphenyl | H | Me | C—(CH₂)₃— | | N | |
| I-148 | H | 3,4-Dimethoxyphenyl | H | OMe | C—(CH₂)₃— | | N | |
| I-149 | H | 3,4-Dimethoxyphenyl | H | Me | C—(CH₂)₂—O | | N | |
| I-150 | H | 3,4-Dimethoxyphenyl | H | OMe | C—(CH₂)₂—O | | N | |
| I-151 | H | 3,4-Dimethoxyphenyl | H | OMe | N | OMe | N | |
| I-152 | H | 3,4-Dimethoxyphenyl | H | NH₂ | N | NH₂ | N | |
| I-153 | H | 3,4-Dimethoxyphenyl | H | NHMe | N | NHMe | N | |
| I-154 | H | 3,4-Dimethoxyphenyl | H | OMe | N | OMe | CH | |
| I-155 | H | 3,4-Dimethoxyphenyl | H | Cl | N | Me | CH | |
| I-156 | H | 3,4-Dimethoxyphenyl | H | OMe | N | N=CH—NH—C | | |
| I-157 | H | 3,4-Dimethoxyphenyl | H | Cl | N | N=CH—NH—C | | |
| I-158 | H | 3,4-Dimethoxyphenyl | H | Me | N | Me | CH | |
| I-159 | H | 3,4-Dimethoxyphenyl | H | OMe | N | Me | CH | |
| I-160 | H | 3,4-Dimethoxyphenyl | H | OMe | N | H | C—NO₂ | |
| I-161 | H | 3,4-Dimethoxyphenyl | H | OMe | C—Me | H | N | |
| I-162 | H | 3,4-Dimethoxyphenyl | H | Me | C—Me | H | N | |
| I-163 | H | 3,4-Dimethoxyphenyl | Me | OMe | CH | OMe | N | |
| I-164 | H | 3,4-Dimethoxyphenyl | Me | OMe | CH | Me | N | |
| I-165 | H | 3,4-Dimethoxyphenyl | Me | Me | CH | Me | N | |
| I-166 | H | 3,4(1,3-Dioxomethylene)phenyl | H | OMe | CH | OMe | N | 228–235 (decomp.) |
| I-167 | H | 3,4(1,3-Dioxomethylene)phenyl | H | OMe | CH | Me | N | |
| I-168 | H | 3,4(1,3-Dioxomethylene)phenyl | H | Me | CH | Me | N | |
| I-169 | H | 3,4(1,3-Dioxomethylene)phenyl | H | Me | CH | Et | N | |
| I-170 | H | 3,4(1,3-Dioxomethylene)phenyl | H | Et | CH | Et | N | |
| I-171 | H | 3,4(1,3-Dioxomethylene)phenyl | H | Me | CH | CF₃ | N | |
| I-172 | H | 3,4(1,3-Dioxomethylene)phenyl | H | OMe | CH | CF₃ | N | |
| I-173 | H | 3,4(1,3-Dioxomethylene)phenyl | H | OMe | CH | H | N | |
| I-174 | H | 3,4(1,3-Dioxomethylene)phenyl | H | SMe | CH | H | N | |
| I-175 | H | 3,4(1,3-Dioxomethylene)phenyl | H | Et | CH | OMe | N | |
| I-176 | H | 3,4(1,3-Dioxomethylene)phenyl | H | Me | C—(CH₂)₃— | | N | |
| I-177 | H | 3,4(1,3-Dioxomethylene)phenyl | H | OMe | C—(CH₂)₃— | | N | |
| I-178 | H | 3,4(1,3-Dioxomethylene)phenyl | H | Me | C—(CH₂)₂—O | | N | |
| I-179 | H | 3,4(1,3-Dioxomethylene)phenyl | H | OMe | C—(CH₂)₂—O | | N | |
| I-180 | H | 3,4(1,3-Dioxomethylene)phenyl | H | OMe | N | OMe | N | |
| I-181 | H | 3,4(1,3-Dioxomethylene)phenyl | H | NH₂ | N | NH₂ | N | |
| I-182 | H | 3,4(1,3-Dioxomethylene)phenyl | H | NHMe | N | NHMe | N | |
| I-183 | H | 3,4(1,3-Dioxomethylene)phenyl | H | OMe | N | OMe | CH | |

TABLE 1-continued (I)

| No. | R⁴ | R⁵ | R⁷ | R² | X | R³ | Y | M.p. [° C.] |
|---|---|---|---|---|---|---|---|---|
| I-184 | H | 3,4(1,3-Dioxomethylene)phenyl | H | Cl | N | Me | CH | |
| I-185 | H | 3,4(1,3-Dioxomethylene)phenyl | H | OMe | N | N=CH—NH—C | | |
| I-186 | H | 3,4(1,3-Dioxomethylene)phenyl | H | Cl | N | N=CH—NH—C | | |
| I-187 | H | 3,4(1,3-Dioxomethylene)phenyl | H | Me | N | Me | CH | |
| I-188 | H | 3,4(1,3-Dioxomethylene)phenyl | H | OMe | N | Me | CH | |
| I-189 | H | 3,4(1,3-Dioxomethylene)phenyl | H | OMe | N | H | C—NO₂ | |
| I-190 | H | 3,4(1,3-Dioxomethylene)phenyl | H | OMe | C—Me | H | N | |
| I-191 | H | 3,4(1,3-Dioxomethylene)phenyl | H | Me | C—Me | H | N | |
| I-192 | H | 3,4(1,3-Dioxomethylene)phenyl | Me | OMe | CH | OMe | N | |
| I-193 | H | 3,4(1,3-Dioxomethylene)phenyl | Me | OMe | CH | Me | N | |
| I-194 | H | 3,4(1,3-Dioxomethylene)phenyl | Me | Me | CH | Me | N | |
| I-195 | Cyclohexyl | Cyclohexyl | H | OMe | CH | OMe | N | |
| I-196 | Cyclohexyl | Cyclohexyl | H | OMe | CH | Me | N | |
| I-197 | Cyclohexyl | Cyclohexyl | H | Me | CH | Me | N | |
| I-198 | Cyclohexyl | Cyclohexyl | H | Me | CH | Et | N | |
| I-199 | Cyclohexyl | Cyclohexyl | H | Et | CH | Et | N | |
| I-200 | Cyclohexyl | Cyclohexyl | H | Me | CH | CF₃ | N | |
| I-201 | Cyclohexyl | Cyclohexyl | H | OMe | CH | CF₃ | N | |
| I-202 | Cyclohexyl | Cyclohexyl | H | OMe | CH | H | N | |
| I-203 | Cyclohexyl | Cyclohexyl | H | SMe | CH | H | N | |
| I-204 | Cyclohexyl | Cyclohexyl | H | Et | CH | OMe | N | |
| I-205 | Cyclohexyl | Cyclohexyl | H | Me | C—(CH₂)₃— | | N | |
| I-206 | Cyclohexyl | Cyclohexyl | H | OMe | C—(CH₂)₃— | | N | |
| I-207 | Cyclohexyl | Cyclohexyl | H | Me | C—(CH₂)₂—O | | N | |
| I-208 | Cyclohexyl | Cyclohexyl | H | OMe | C—(CH₂)₂—O | | N | |
| I-209 | Cyclohexyl | Cyclohexyl | H | OMe | N | OMe | N | |
| I-210 | Cyclohexyl | Cyclohexyl | H | NH₂ | N | NH₂ | N | |
| I-211 | Cyclohexyl | Cyclohexyl | H | NHMe | N | NHMe | N | |
| I-212 | Cyclohexyl | Cyclohexyl | H | OMe | N | OMe | CH | |
| I-213 | Cyclohexyl | Cyclohexyl | H | Cl | N | Me | CH | |
| I-214 | Cyclohexyl | Cyclohexyl | H | OMe | N | N=CH—NH—C | | |
| I-215 | Cyclohexyl | Cyclohexyl | H | Cl | N | N=CH—NH—C | | |
| I-216 | Cyclohexyl | Cyclohexyl | H | Me | N | Me | CH | |
| I-217 | Cyclohexyl | Cyclohexyl | H | OMe | N | Me | CH | |
| I-218 | Cyclohexyl | Cyclohexyl | H | OMe | N | H | C—NO₂ | |
| I-219 | Cyclohexyl | Cyclohexyl | H | OMe | C—Me | H | N | |
| I-220 | Cyclohexyl | Cyclohexyl | H | Me | C—Me | H | N | |
| I-221 | Cyclohexyl | Cyclohexyl | Me | OMe | CH | OMe | N | |
| I-222 | Cyclohexyl | Cyclohexyl | Me | OMe | CH | Me | N | |
| I-223 | Cyclohexyl | Cyclohexyl | Me | Me | CH | Me | N | |
| I-224 | H | p-Phenylphenyl | H | OMe | CH | OMe | N | |
| I-225 | H | p-Phenylphenyl | H | OMe | CH | Me | N | |
| I-226 | H | p-Phenylphenyl | H | Me | CH | Me | N | |
| I-227 | H | p-Phenylphenyl | H | Me | CH | Et | N | |
| I-228 | H | p-Phenylphenyl | H | Et | CH | Et | N | |
| I-229 | H | p-Phenylphenyl | H | Me | CH | CF₃ | N | |
| I-230 | H | p-Phenylphenyl | H | OMe | CH | CF₃ | N | |
| I-231 | H | p-Phenylphenyl | H | OMe | CH | H | N | |
| I-232 | H | p-Phenylphenyl | H | SMe | CH | H | N | |
| I-233 | H | p-Phenylphenyl | H | Et | CH | OMe | N | |
| I-234 | H | p-Phenylphenyl | H | Me | C—(CH₂)₃— | | N | |
| I-235 | H | p-Phenylphenyl | H | OMe | C—(CH₂)₃— | | N | |
| I-236 | H | p-Phenylphenyl | H | Me | C—(CH₂)₂—O | | N | |
| I-237 | H | p-Phenylphenyl | H | OMe | C—(CH₂)₂—O | | N | |
| I-238 | H | p-Phenylphenyl | H | OMe | N | OMe | N | |

TABLE 1-continued

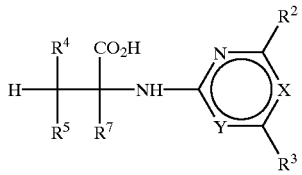

(I)

| No. | R⁴ | R⁵ | R⁷ | R² | X | R³ | Y | M.p. [° C.] |
|---|---|---|---|---|---|---|---|---|
| I-239 | H | p-Phenylphenyl | H | NH₂ | N | NH₂ | N | |
| I-240 | H | p-Phenylphenyl | H | NHMe | N | MHMe | N | |
| I-241 | H | p-Phenylphenyl | H | OMe | N | OMe | CH | |
| I-242 | H | p-Phenylphenyl | H | Cl | N | Me | CH | |
| I-243 | H | p-Phenylphenyl | H | OMe | N | N=CH—NH—C | | |
| I-244 | H | p-Phenylphenyl | H | Cl | N | N=CH—NH—C | | |
| I-245 | H | p-Phenylphenyl | H | Me | N | Me | CH | |
| I-246 | H | p-Phenylphenyl | H | OMe | N | Me | CH | |
| I-247 | H | p-Phenylphenyl | H | OMe | N | H | C—NO₂ | |
| I-248 | H | p-Phenylphenyl | H | OMe | C—Me | H | N | |
| I-249 | H | p-Phenylphenyl | H | Me | C—Me | H | N | |
| I-250 | H | p-Phenylphenyl | Me | OMe | CH | OMe | N | |
| I-251 | H | p-Phenylphenyl | Me | OMe | CH | Me | N | |
| I-252 | H | p-Phenylphenyl | Me | Me | CH | Me | N | |
| I-253 | Phenyl | Phenyl | H | OMe | CH | OMe | N | 69 |
| I-254 | Phenyl | Phenyl | H | OMe | CH | Me | N | |
| I-255 | Phenyl | Phenyl | H | Me | CH | Me | N | 172–174 |
| I-256 | Phenyl | Phenyl | H | Me | CH | Et | N | |
| I-257 | Phenyl | Phenyl | H | Et | CH | Et | N | |
| I-258 | Phenyl | Phenyl | H | Me | CH | CF₃ | N | |
| I-259 | Phenyl | Phenyl | H | OMe | CH | CF₃ | N | |
| I-260 | Phenyl | Phenyl | H | OMe | CH | H | N | |
| I-261 | Phenyl | Phenyl | H | SMe | CH | H | N | |
| I-262 | Phenyl | Phenyl | H | Et | CH | OMe | N | |
| I-263 | Phenyl | Phenyl | H | CF₃ | CH | H | N | 203–208 |
| I-264 | Phenyl | Phenyl | H | Me | CH | H | N | |
| I-265 | Phenyl | Phenyl | H | Me | C—(CH₂)₃— | | N | |
| I-266 | Phenyl | Phenyl | H | OMe | C—(CH₂)₃— | | N | |
| I-267 | Phenyl | Phenyl | H | Me | C—(CH₂)₂—O | | N | |
| I-268 | Phenyl | Phenyl | H | OMe | C—(CH₂)₂—O | | N | |
| I-269 | Phenyl | Phenyl | H | OMe | N | OMe | N | 172–175 |
| I-270 | Phenyl | Phenyl | H | NH₂ | N | NH₂ | N | |
| I-271 | Phenyl | Phenyl | H | NHMe | N | NHMe | N | |
| I-272 | Phenyl | Phenyl | H | Me | N | Me | N | |
| I-273 | Phenyl | Phenyl | H | SMe | N | SMe | N | 68–75 |
| I-274 | Phenyl | Phenyl | H | H | CH | H | N | |
| I-275 | Phenyl | Phenyl | H | OMe | N | OMe | CH | |
| I-276 | Phenyl | Phenyl | H | Cl | N | Me | CH | |
| I-277 | Phenyl | Phenyl | H | OMe | N | N=CH—NH—C | | |
| I-278 | Phenyl | Phenyl | H | Cl | N | N=CH—NH—C | | |
| I-279 | Phenyl | Phenyl | H | H | N | N=CH—NH—C | | |
| I-280 | Phenyl | Phenyl | H | SMe | N | H | CH | |
| I-281 | Phenyl | Phenyl | H | CMe₃ | N | CF₃ | CH | 56–63 |
| I-282 | Phenyl | Phenyl | H | OMe | N | Me | CH | |
| I-283 | Phenyl | Phenyl | H | OMe | N | H | C—NO₂ | |
| I-284 | Phenyl | Phenyl | H | OMe | C—Me | H | N | |
| I-285 | Phenyl | Phenyl | H | Me | C—Me | H | N | |
| I-286 | Phenyl | Phenyl | H | OMe | CH | H | C—NO₂ | 172–180 |
| I-287 | Phenyl | Phenyl | H | Me | CH | H | C—NO₂ | |
| I-288 | Phenyl | Phenyl | H | OMe | CH | H | C—NH₂ | |
| I-289 | Phenyl | Phenyl | H | OMe | C—NO₂ | OMe | CH | |
| I-290 | Phenyl | Phenyl | H | OMe | C—NO₂ | H | CH | |
| I-291 | Phenyl | Phenyl | H | Me | C—NO₂ | Me | CH | |
| I-292 | Phenyl | Phenyl | H | Me | C—NH₂ | Me | CH | |
| I-293 | Phenyl | Phenyl | H | Me | C—NO₂ | OMe | CH | |
| I-294 | Phenyl | Phenyl | H | Me | C—NH₂ | OMe | CH | |
| I-295 | Phenyl | Phenyl | Me | OMe | CH | OMe | N | |
| I-296 | Phenyl | Phenyl | Me | OMe | CH | Me | N | |
| I-297 | Phenyl | Phenyl | Me | Me | CH | Me | N | |
| I-298 | Phenyl | Phenyl | Me | OMe | N | OMe | N | |
| I-299 | 3-Methoxyphenyl | 3-Methoxyphenyl | H | OMe | CH | OMe | N | 58–66 |
| I-300 | 3-Methoxyphenyl | 3-Methoxyphenyl | H | OMe | CH | Me | N | |
| I-301 | 3-Methoxyphenyl | 3-Methoxyphenyl | H | Me | CH | Me | N | |
| I-302 | 3-Methoxyphenyl | 3-Methoxyphenyl | H | Me | CH | Et | N | |
| I-303 | 3-Methoxyphenyl | 3-Methoxyphenyl | H | Et | CH | Et | N | |
| I-304 | 3-Methoxyphenyl | 3-Methoxyphenyl | H | Me | CH | CF₃ | N | |

TABLE 1-continued

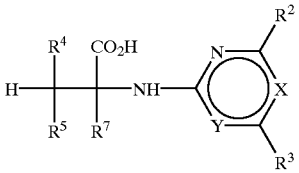
(I)

| No. | R⁴ | R⁵ | R⁷ | R² | X | R³ | Y | M.p. [° C.] |
|---|---|---|---|---|---|---|---|---|
| I-305 | 3-Methoxyphenyl | 3-Methoxyphenyl | H | OMe | CH | CF₃ | N | |
| I-306 | 3-Methoxyphenyl | 3-Methoxyphenyl | H | OMe | CH | H | N | |
| I-307 | 3-Methoxyphenyl | 3-Methoxyphenyl | H | SMe | CH | H | N | |
| I-308 | 3-Methoxyphenyl | 3-Methoxyphenyl | H | Et | CH | OMe | N | |
| I-309 | 3-Methoxyphenyl | 3-Methoxyphenyl | H | Me | C—(CH₂)₃— | | N | |
| I-310 | 3-Methoxyphenyl | 3-Methoxyphenyl | H | OMe | C—(CH₂)₃— | | N | |
| I-311 | 3-Methoxyphenyl | 3-Methoxyphenyl | H | Me | C—(CH₂)₂—O | | N | |
| I-312 | 3-Methoxyphenyl | 3-Methoxyphenyl | H | OMe | C—(CH₂)₂—O | | N | |
| I-313 | 3-Methoxyphenyl | 3-Methoxyphenyl | H | OMe | N | OMe | N | |
| I-314 | 3-Methoxyphenyl | 3-Methoxyphenyl | H | NH₂ | N | NH₂ | N | |
| I-315 | 3-Methoxyphenyl | 3-Methoxyphenyl | H | NHMe | N | NHMe | N | |
| I-316 | 3-Methoxyphenyl | 3-Methoxyphenyl | H | OMe | N | OMe | CH | |
| I-317 | 3-Methoxyphenyl | 3-Methoxyphenyl | H | Cl | N | Me | CH | |
| I-318 | 3-Methoxyphenyl | 3-Methoxyphenyl | H | OMe | N | N=CH—NH—C | | |
| I-319 | 3-Methoxyphenyl | 3-Methoxyphenyl | H | Cl | N | N=CH—NH—C | | |
| I-320 | 3-Methoxyphenyl | 3-Methoxyphenyl | H | Me | N | Me | CH | |
| I-321 | 3-Methoxyphenyl | 3-Methoxyphenyl | H | OMe | N | Me | CH | |
| I-322 | 3-Methoxyphenyl | 3-Methoxyphenyl | H | OMe | N | H | C—NO₂ | |
| I-323 | 3-Methoxyphenyl | 3-Methoxyphenyl | H | OMe | C—Me | H | N | |
| I-324 | 3-Methoxyphenyl | 3-Methoxyphenyl | H | Me | C—Me | H | N | |
| I-325 | 3-Methoxyphenyl | 3-Methoxyphenyl | Me | OMe | CH | OMe | N | |
| I-326 | 3-Methoxyphenyl | 3-Methoxyphenyl | Me | OMe | CH | Me | N | |
| I-327 | 3-Methoxyphenyl | 3-Methoxyphenyl | Me | Me | CH | Me | N | |
| I-328 | 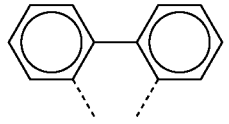 | | H | OMe | N | OMe | N | 182–186 |
| I-329 | 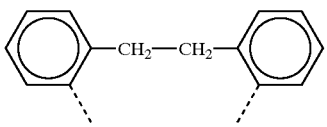 | | H | OMe | CH | OMe | N | |
| I-330 | 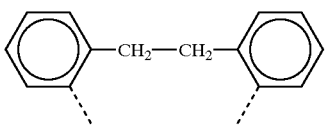 | | H | Me | CH | Me | N | |
| I-331 | 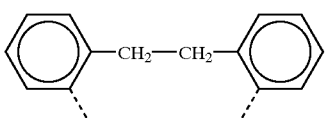 | | H | Me | CH | OMe | N | |
| I-332 | 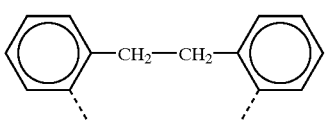 | | H | OMe | C—Me | H | N | |
| I-333 | 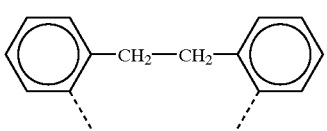 | | H | OMe | CH | H | N | |

TABLE 1-continued (I)

| No. | R⁴ | R⁵ | R⁷ | R² | X | R³ | Y | M.p. [° C.] |
|---|---|---|---|---|---|---|---|---|
| I-334 | –C₆H₄–CH₂–CH₂–C₆H₄– (bridging R⁴ and R⁵, ortho linkage) | | H | OMe | N | OMe | CH | |

TABLE 2

I

| No. | R⁴ | R⁵ | R⁷ | R² | X | R³ | Y | M.p. [° C.] |
|---|---|---|---|---|---|---|---|---|
| I-335 | Phenyl | Phenyl | H | OMe | CH | OMe | N | |
| I-336 | Phenyl | Phenyl | H | OMe | CH | Me | N | |
| I-337 | Phenyl | Phenyl | H | Me | CH | Me | N | |
| I-338 | Phenyl | Phenyl | H | Me | CH | Et | N | |
| I-339 | Phenyl | Phenyl | H | Et | CH | Et | N | |
| I-340 | Phenyl | Phenyl | H | Me | CH | CF₃ | N | |
| I-341 | Phenyl | Phenyl | H | OMe | CH | CF₃ | N | |
| I-342 | Phenyl | Phenyl | H | OMe | CH | H | N | |
| I-343 | Phenyl | Phenyl | H | SMe | CH | H | N | |
| I-344 | Phenyl | Phenyl | H | Et | CH | OMe | N | |
| I-345 | Phenyl | Phenyl | H | CF₃ | CH | H | N | |
| I-346 | Phenyl | Phenyl | H | Me | CH | H | N | |
| I-347 | Phenyl | Phenyl | H | Me | C—(CH₂)₃— | | N | |
| I-348 | Phenyl | Phenyl | Me | OMe | C—(CH₂)₃— | | CH | |
| I-349 | Phenyl | Phenyl | Me | Me | C—(CH₂)₂—O | | N | |
| I-350 | Phenyl | Phenyl | Me | OMe | C—(CH₂)₂—O | | N | |
| I-351 | Phenyl | Phenyl | H | OMe | N | OMe | N | |
| I-352 | Phenyl | Phenyl | H | NH₂ | N | NH₂ | N | |
| I-353 | Phenyl | Phenyl | H | NHMe | N | NHMe | N | |
| I-354 | Phenyl | Phenyl | H | Me | N | Me | N | |
| I-355 | Phenyl | Phenyl | H | SMe | N | SMe | N | |
| I-356 | Phenyl | Phenyl | H | H | CH | H | N | |
| I-357 | Phenyl | Phenyl | H | OMe | N | OMe | CH | |
| I-358 | Phenyl | Phenyl | H | Cl | N | Me | CH | |
| I-359 | Phenyl | Phenyl | H | OMe | N | N=CH—NH—C | | |
| I-360 | Phenyl | Phenyl | H | Cl | N | N=CH—NH—C | | |
| I-361 | Phenyl | Phenyl | H | H | N | N=CH—NH—C | | |
| I-362 | Phenyl | Phenyl | H | SMe | N | H | CH | |
| I-363 | Phenyl | Phenyl | H | CMe₃ | N | CF₃ | CH | |
| I-364 | Phenyl | Phenyl | H | OMe | N | Me | CH | |
| I-365 | Phenyl | Phenyl | H | OMe | N | H | C—NO₂ | |
| I-366 | Phenyl | Phenyl | H | OMe | C—Me | H | N | |
| I-367 | Phenyl | Phenyl | H | Me | C—Me | H | N | |
| I-368 | Phenyl | Phenyl | H | OMe | CH | H | C—NO₂ | |
| I-369 | Phenyl | Phenyl | H | Me | CH | H | C—NO₂ | |
| I-370 | Phenyl | Phenyl | H | OMe | CH | H | C—NH₂ | |
| I-371 | Phenyl | Phenyl | H | OMe | C—NO₂ | OMe | CH | |
| I-372 | Phenyl | Phenyl | H | OMe | C—NO₂ | H | CH | |
| I-373 | Phenyl | Phenyl | H | Me | C—NO₂ | Me | CH | |
| I-374 | Phenyl | Phenyl | H | Me | C—NH₂ | Me | CH | |
| I-375 | Phenyl | Phenyl | H | Me | C—NO₂ | OMe | CH | |
| I-376 | Phenyl | Phenyl | H | Me | C—NH₂ | OMe | CH | |
| I-377 | Phenyl | Phenyl | Me | OMe | CH | OMe | N | |

TABLE 2-continued

I

| No. | R⁴ | R⁵ | R⁷ | R² | X | R³ | Y | M.p. [° C.] |
|---|---|---|---|---|---|---|---|---|
| I-378 | Phenyl | Phenyl | Me | OMe | CH | Me | N | |
| I-379 | Phenyl | Phenyl | Me | Me | CH | Me | N | |
| I-380 | Phenyl | Phenyl | Me | OMe | N | OMe | N | |
| I-381 | Me | Phenyl | H | OMe | CH | OMe | N | |
| I-382 | Me | Phenyl | H | OMe | CH | Me | N | |
| I-383 | Me | Phenyl | H | Me | CH | Me | N | |
| I-384 | Me | Phenyl | H | Me | CH | Et | N | |
| I-385 | Me | Phenyl | H | Et | CH | Et | N | |
| I-386 | Me | Phenyl | H | Me | CH | CF₃ | N | |
| I-387 | Me | Phenyl | H | OMe | CH | CF₃ | N | |
| I-388 | Me | Phenyl | H | OMe | CH | H | N | |
| I-389 | Me | Phenyl | H | SMe | CH | H | N | |
| I-390 | Me | Phenyl | H | Et | CH | OMe | N | |
| I-391 | Me | Phenyl | H | CF₃ | CH | H | N | |
| I-392 | Me | Phenyl | H | Me | CH | H | N | |
| I-393 | Me | Phenyl | H | Me | C—(CH₂)₃— | | N | |
| I-394 | Me | Phenyl | H | OMe | C—(CH₂)₃— | | N | |
| I-395 | Me | Phenyl | H | Me | C—(CH₂)₂—O | | N | |
| I-396 | Me | Phenyl | H | OMe | C—(CH₂)₂—O | | N | |
| I-397 | Me | Phenyl | H | OMe | N | OMe | N | |
| I-398 | Me | Phenyl | H | NH₂ | N | NH₂ | N | |
| I-399 | Me | Phenyl | H | NHMe | N | NHMe | N | |
| I-400 | Me | Phenyl | H | Me | N | Me | N | |
| I-401 | Me | Phenyl | H | SMe | N | SMe | N | |
| I-402 | Me | Phenyl | H | H | CH | H | N | |
| I-403 | Me | Phenyl | H | OMe | N | OMe | CH | |
| I-404 | Me | Phenyl | H | Cl | N | Me | CH | |
| I-405 | Me | Phenyl | H | OMe | N | N=CH—NH—C | | |
| I-406 | Me | Phenyl | H | Cl | N | N=CH—NH—C | | |
| I-407 | Me | Phenyl | H | H | N | N=CH—NH—C | | |
| I-408 | Me | Phenyl | H | SMe | N | H | CH | |
| I-409 | Me | Phenyl | H | CMe₃ | N | CF₃ | CH | |
| I-410 | Me | Phenyl | H | OMe | N | Me | CH | |
| I-411 | Me | Phenyl | H | OMe | N | H | C—NO₂ | |
| I-412 | Me | Phenyl | H | OMe | C—Me | H | N | |
| I-413 | Me | Phenyl | H | Me | C—Me | H | N | |
| I-414 | Me | Phenyl | H | OMe | CH | H | C—NO₂ | |
| I-415 | Me | Phenyl | H | Me | CH | H | C—NO₂ | |
| I-416 | Me | Phenyl | H | OMe | CH | H | C—NH₂ | |
| I-417 | Me | Phenyl | H | OMe | C—NO₂ | OMe | CH | |
| I-418 | Me | Phenyl | H | OMe | C—NO₂ | H | CH | |
| I-419 | Me | Phenyl | H | Me | C—NO₂ | Me | CH | |
| I-420 | Me | Phenyl | H | Me | C—NH₂ | Me | CH | |
| I-421 | Me | Phenyl | H | Me | C—NO₂ | OMe | CH | |
| I-422 | Me | Phenyl | H | Me | C—NH₂ | OMe | CH | |
| I-423 | Me | Phenyl | Me | OMe | CH | OMe | N | |
| I-424 | Me | Phenyl | Me | OMe | CH | Me | N | |
| I-425 | Me | Phenyl | Me | Me | CH | Me | N | |
| I-426 | Me | Phenyl | Me | OMe | N | OMe | N | |
| I-427 | Me | 3,4(1,3-Dioxomethylene)phenyl | H | OMe | CH | OMe | N | |
| I-428 | Me | 3,4(1,3-Dioxomethylene)phenyl | H | OMe | CH | Me | N | |
| I-429 | Me | 3,4(1,3-Dioxomethylene)phenyl | H | Me | CH | Me | N | |
| I-430 | Me | 3,4(1,3-Dioxomethylene)phenyl | H | Me | CH | Et | N | |
| I-431 | Me | 3,4(1,3-Dioxomethylene)phenyl | H | Et | CH | Et | N | |
| I-432 | Me | 3,4(1,3-Dioxomethylene)phenyl | H | Me | CH | CF₃ | N | |
| I-433 | Me | 3,4(1,3-Dioxomethylene)phenyl | H | OMe | CH | CF₃ | N | |
| I-434 | Me | 3,4(1,3-Dioxomethylene)phenyl | H | OMe | CH | H | N | |
| I-435 | Me | 3,4(1,3-Dioxomethylene)phenyl | H | SMe | CH | H | N | |

TABLE 2-continued

Structure I: CH₃—C(R⁴)(R⁵)—C(R⁷)(CO₂H)—NH—[pyrimidine with R², X, R³, Y]

| No. | R⁴ | R⁵ | R⁷ | R² | X | R³ | Y | M.p. [° C.] |
|---|---|---|---|---|---|---|---|---|
| I-436 | Me | 3,4(1,3-Dioxomethylene)phenyl | H | Et | CH | OMe | N | |
| I-437 | Me | 3,4(1,3-Dioxomethylene)phenyl | H | $CF_3$ | CH | H | N | |
| I-438 | Me | 3,4(1,3-Dioxomethylene)phenyl | H | Me | CH | H | N | |
| I-439 | Me | 3,4(1,3-Dioxomethylene)phenyl | H | Me | C—$(CH_2)_3$— | | N | |
| I-440 | Me | 3,4(1,3-Dioxomethylene)phenyl | H | OMe | C—$(CH_2)_3$— | | N | |
| I-441 | Me | 3,4(1,3-Dioxomethylene)phenyl | H | Me | C—$(CH_2)_2$—O | | N | |
| I-442 | Me | 3,4(1,3-Dioxomethylene)phenyl | H | OMe | C—$(CH_2)_2$—O | | N | |
| I-443 | Me | 3,4(1,3-Dioxomethylene)phenyl | H | OMe | N | OMe | N | |
| I-444 | Me | 3,4(1,3-Dioxomethylene)phenyl | H | $NH_2$ | N | $NH_2$ | N | |
| I-445 | Me | 3,4(1,3-Dioxomethylene)phenyl | H | NHMe | N | NHMe | N | |
| I-446 | Me | 3,4(1,3-Dioxomethylene)phenyl | H | Me | N | Me | N | |
| I-447 | Me | 3,4(1,3-Dioxomethylene)phenyl | H | SMe | N | SMe | N | |
| I-448 | Me | 3,4(1,3-Dioxomethylene)phenyl | H | H | CH | H | N | |
| I-449 | Me | 3,4(1,3-Dioxomethylene)phenyl | H | OMe | N | OMe | CH | |
| I-450 | Me | 3,4(1,3-Dioxomethylene)phenyl | H | Cl | N | Me | CH | |
| I-451 | Me | 3,4(1,3-Dioxomethylene)phenyl | H | OMe | N | N=CH—NH—C | | |
| I-452 | Me | 3,4(1,3-Dioxomethylene)phenyl | H | Cl | N | N=CH—NH—C | | |
| I-453 | Me | 3,4(1,3-Dioxomethylene)phenyl | H | H | N | N=CH—NH—C | | |
| I-454 | Me | 3,4(1,3-Dioxomethylene)phenyl | H | SMe | N | H | CH | |
| I-455 | Me | 3,4(1,3-Dioxomethylene)phenyl | H | $CMe_3$ | N | $CF_3$ | CH | |
| I-456 | Me | 3,4(1,3-Dioxomethylene)phenyl | H | OMe | N | Me | CH | |
| I-457 | Me | 3,4(1,3-Dioxomethylene)phenyl | H | OMe | N | H | C—$NO_2$ | |
| I-458 | Me | 3,4(1,3-Dioxomethylene)phenyl | H | OMe | C—Me | H | N | |
| I-459 | Me | 3,4(1,3-Dioxomethylene)phenyl | H | Me | C—Me | H | N | |
| I-460 | Me | 3,4(1,3-Dioxomethylene)phenyl | H | OMe | CH | H | C—$NO_2$ | |
| I-461 | Me | 3,4(1,3-Dioxomethylene)phenyl | H | Me | CH | H | C—$NO_2$ | |
| I-462 | Me | 3,4(1,3-Dioxomethylene)phenyl | H | OMe | CH | H | C—$NH_2$ | |
| I-463 | Me | 3,4(1,3-Dioxomethylene)phenyl | H | OMe | C—$NO_2$ | OMe | CH | |
| I-464 | Me | 3,4(1,3-Dioxomethylene)phenyl | H | OMe | C—$NO_2$ | H | CH | |
| I-465 | Me | 3,4(1,3-Dioxomethylene)phenyl | H | Me | C—$NO_2$ | Me | CH | |
| I-466 | Me | 3,4(1,3-Dioxomethylene)phenyl | H | Me | C—$NH_2$ | Me | CH | |
| I-467 | Me | 3,4(1,3-Dioxomethylene)phenyl | H | Me | C—$NO_2$ | OMe | CH | |
| I-468 | Me | 3,4(1,3-Dioxomethylene)phenyl | H | Me | C—$NH_2$ | OMe | CH | |

TABLE 2-continued $$\text{structure I: } CH_3-C(R^4)(R^5)-C(R^7)(CO_2H)-NH-\text{pyrimidine}(R^2, X, Y, R^3)$$

| No. | R⁴ | R⁵ | R⁷ | R² | X | R³ | Y | M.p. [° C.] |
|---|---|---|---|---|---|---|---|---|
| I-469 | Me | 3,4(1,3-Dioxomethylene)phenyl | Me | OMe | CH | OMe | N | |
| I-470 | Me | 3,4(1,3-Dioxomethylene) phenyl | Me | OMe | CH | Me | N | |
| I-471 | Me | 3,4(1,3-Dioxomethylene)phenyl | Me | Me | CH | Me | N | |
| I-472 | Me | 3,4(1,3-Dioxomethylene)phenyl | Me | OMe | N | OMe | N | |
| I-473 | Me | 3,4-Dimethoxyphenyl | H | OMe | N | OMe | N | |
| I-474 | Me | 3,4-Dimethoxyphenyl | H | OMe | CH | OMe | N | |
| I-475 | Me | 3,4-Dimethoxyphenyl | H | Me | CH | OMe | N | |
| I-476 | Me | 3,4-Dimethoxyphenyl | H | Me | CH | Me | N | |
| I-477 | Me | 3,4-Dimethoxyphenyl | H | OMe | N | OMe | CH | |
| I-478 | Me | 3,4-Dimethoxyphenyl | Me | OMe | CH | OMe | N | |
| I-479 | Me | 3,4-Dimethoxyphenyl | Me | OMe | N | OMe | N | |
| I-480 | Me | 3,4-Dimethoxyphenyl | H | OMe | CH | H | N | |
| I-481 | Me | 3,4-Dimethoxyphenyl | H | OMe | C—Me | H | N | |
| I-482 | Me | 4-Methoxyphenyl | H | OMe | CH | OMe | N | |
| I-483 | Me | 4-Methoxyphenyl | H | Me | CH | OMe | N | |
| I-484 | Me | 4-Methoxyphenyl | H | Me | CH | Me | N | |
| I-485 | Me | 4-Methoxyphenyl | H | OMe | N | OMe | CH | |
| I-486 | Me | 4-Methoxyphenyl | H | OMe | CH | H | N | |
| I-487 | Me | 4-Methoxyphenyl | H | OMe | C—Me | H | N | |
| I-488 | Me | 4-Methoxyphenyl | H | OMe | N | OMe | N | |
| I-489 | Me | 4-Methoxyphenyl | Me | OMe | CH | OMe | N | |
| I-490 | Me | 4-Methoxyphenyl | Me | OMe | N | OMe | N | |
| I-491 | Me | 3-Methoxyphenyl | H | OMe | CH | OMe | N | |
| I-492 | Me | 3-Methoxyphenyl | H | Me | CH | OMe | N | |
| I-493 | Me | 3-Methoxyphenyl | H | Me | CH | Me | N | |
| I-494 | Me | 3-Methoxyphenyl | H | OMe | N | OMe | CH | |
| I-495 | Me | 3-Methoxyphenyl | H | OMe | CH | H | N | |
| I-496 | Me | 3-Methoxyphenyl | H | OMe | C—Me | H | N | |
| I-497 | Me | 3-Methoxyphenyl | H | OMe | N | OMe | N | |
| I-498 | Me | 3-Methoxyphenyl | Me | OMe | CH | OMe | N | |
| I-499 | Me | 3-Methoxyphenyl | Me | OMe | N | OMe | N | |
| I-500 | 4-Methoxyphenyl | 4-Methoxyphenyl | H | OMe | CH | OMe | N | |
| I-501 | 4-Methoxyphenyl | 4-Methoxyphenyl | H | OMe | CH | Me | N | |
| I-502 | 4-Methoxyphenyl | 4-Methoxyphenyl | H | Me | CH | Me | N | |
| I-503 | 4-Methoxyphenyl | 4-Methoxyphenyl | H | Me | CH | Et | N | |
| I-504 | 4-Methoxyphenyl | 4-Methoxyphenyl | H | Et | CH | Et | N | |
| I-505 | 4-Methoxyphenyl | 4-Methoxyphenyl | H | Me | CH | CF₃ | N | |
| I-506 | 4-Methoxyphenyl | 4-Methoxyphenyl | H | OMe | CH | CF₃ | N | |
| I-507 | 4-Methoxyphenyl | 4-Methoxyphenyl | H | OMe | CH | H | N | |
| I-508 | 4-Methoxyphenyl | 4-Methoxyphenyl | H | SMe | CH | H | N | |
| I-509 | 4-Methoxyphenyl | 4-Methoxyphenyl | H | Et | CH | OMe | N | |
| I-510 | 4-Methoxyphenyl | 4-Methoxyphenyl | H | CF₃ | CH | H | N | |
| I-511 | 4-Methoxyphenyl | 4-Methoxyphenyl | H | Me | CH | H | N | |
| I-512 | 4-Methoxyphenyl | 4-Methoxyphenyl | H | Me | C—(CH₂)₃— | | N | |
| I-513 | 4-Methoxyphenyl | 4-Methoxyphenyl | H | OMe | C—(CH₂)₃— | | N | |
| I-514 | 4-Methoxyphenyl | 4-Methoxyphenyl | H | Me | C—(CH₂)₂—O | | N | |
| I-515 | 4-Methoxyphenyl | 4-Methoxyphenyl | H | OMe | C—(CH₂)₂—O | | N | |
| I-516 | 4-Methoxyphenyl | 4-Methoxyphenyl | H | OMe | N | OMe | N | |
| I-517 | 4-Methoxyphenyl | 4-Methoxyphenyl | H | NH₂ | N | NH₂ | N | |
| I-518 | 4-Methoxyphenyl | 4-Methoxyphenyl | H | NHMe | N | NHMe | N | |
| I-519 | 4-Methoxyphenyl | 4-Methoxyphenyl | H | Me | N | Me | N | |
| I-520 | 4-Methoxyphenyl | 4-Methoxyphenyl | H | SMe | N | SMe | N | |
| I-521 | 4-Methoxyphenyl | 4-Methoxyphenyl | H | H | CH | H | N | |
| I-522 | 4-Methoxyphenyl | 4-Methoxyphenyl | H | OMe | N | OMe | CH | |
| I-523 | 4-Methoxyphenyl | 4-Methoxyphenyl | H | Cl | N | Me | CH | |
| I-524 | 4-Methoxyphenyl | 4-Methoxyphenyl | H | OMe | N | N=CH—NH—C | | |
| I-525 | 4-Methoxyphenyl | 4-Methoxyphenyl | H | Cl | N | N=CH—NH—C | | |
| I-526 | 4-Methoxyphenyl | 4-Methoxyphenyl | H | H | N | N=CH—NH—C | | |
| I-527 | 4-Methoxyphenyl | 4-Methoxyphenyl | H | SMe | N | H | CH | |
| I-528 | 4-Methoxyphenyl | 4-Methoxyphenyl | H | CMe₃ | N | CF₃ | CH | |
| I-529 | 4-Methoxyphenyl | 4-Methoxyphenyl | H | OMe | N | Me | CH | |

TABLE 2-continued

I

| No. | R⁴ | R⁵ | R⁷ | R² | X | R³ | Y | M.p. [° C.] |
|---|---|---|---|---|---|---|---|---|
| I-530 | 4-Methoxyphenyl | 4-Methoxyphenyl | H | OMe | N | H | C—NO₂ | |
| I-531 | 4-Methoxyphenyl | 4-Methoxyphenyl | H | OMe | C—Me | H | N | |
| I-532 | 4-Methoxyphenyl | 4-Methoxyphenyl | H | Me | C—Me | H | N | |
| I-533 | 4-Methoxyphenyl | 4-Methoxyphenyl | H | OMe | CH | H | C—NO₂ | |
| I-534 | 4-Methoxyphenyl | 4-Methoxyphenyl | H | Me | CH | H | C—NO₂ | |
| I-535 | 4-Methoxyphenyl | 4-Methoxyphenyl | H | OMe | CH | H | C—NH₂ | |
| I-536 | 4-Methoxyphenyl | 4-Methoxyphenyl | H | OMe | C—NO₂ | OMe | CH | |
| I-537 | 4-Methoxyphenyl | 4-Methoxyphenyl | H | OMe | C—NO₂ | H | CH | |
| I-538 | 4-Methoxyphenyl | 4-Methoxyphenyl | H | Me | C—NO₂ | Me | CH | |
| I-539 | 4-Methoxyphenyl | 4-Methoxyphenyl | H | Me | C—NH₂ | Me | CH | |
| I-540 | 4-Methoxyphenyl | 4-Methoxyphenyl | H | Me | C—NO₂ | OMe | CH | |
| I-541 | 4-Methoxyphenyl | 4-Methoxyphenyl | H | Me | C—NH₂ | OMe | CH | |
| I-542 | 4-Methoxyphenyl | 4-Methoxyphenyl | Me | OMe | CH | OMe | N | |
| I-543 | 4-Methoxyphenyl | 4-Methoxyphenyl | Me | OMe | CH | Me | N | |
| I-544 | 4-Methoxyphenyl | 4-Methoxyphenyl | Me | Me | CH | Me | N | |
| I-545 | 4-Methoxyphenyl | 4-Methoxyphenyl | Me | OMe | N | OMe | N | |

TABLE 3

I

| No. | R⁴ | R⁵ | R⁷ | R² | X | R³ | Y | M.p. [° C.] |
|---|---|---|---|---|---|---|---|---|
| I-546 | Phenyl | Phenyl | H | OMe | CH | OMe | N | |
| I-547 | Phenyl | Phenyl | H | OMe | CH | Me | N | |
| I-548 | Phenyl | Phenyl | H3 | Me | CH | Me | N | |
| I-549 | Phenyl | Phenyl | H | Me | CH | Et | N | |
| I-550 | Phenyl | Phenyl | H | Et | CH | Et | N | |
| I-551 | Phenyl | Phenyl | H | Me | CH | CF₃ | N | |
| I-552 | Phenyl | Phenyl | H | OMe | CH | CF₃ | N | |
| I-553 | Phenyl | Phenyl | H | OMe | CH | H | N | |
| I-554 | Phenyl | Phenyl | H | SMe | CH | H | N | |
| I-555 | Phenyl | Phenyl | H | Et | CH | OMe | N | |
| I-556 | Phenyl | Phenyl | H | CF₃ | CH | H | N | |
| I-557 | Phenyl | Phenyl | H | Me | CH | H | N | |
| I-558 | Phenyl | Phenyl | H | Me | C—(CH₂)₃— | | N | |
| I-559 | Phenyl | Phenyl | Me | OMe | C—(CH₂)₃— | | CH | |
| I-560 | Phenyl | Phenyl | Me | Me | C—(CH₂)₂—O | | N | |
| I-561 | Phenyl | Phenyl | Me | OMe | C—(CH₂)₂—O | | N | |
| I-562 | Phenyl | Phenyl | H | OMe | N | OMe | N | |
| I-563 | Phenyl | Phenyl | H | NH₂ | N | NH₂ | N | |
| I-564 | Phenyl | Phenyl | H | NHMe | N | NHMe | N | |
| I-565 | Phenyl | Phenyl | H | Me | N | Me | N | |
| I-566 | Phenyl | Phenyl | H | SMe | N | SMe | N | |
| I-567 | Phenyl | Phenyl | H | H | CH | H | N | |
| I-568 | Phenyl | Phenyl | H | OMe | N | OMe | CH | |
| I-569 | Phenyl | Phenyl | H | Cl | N | Me | CH | |
| I-570 | Phenyl | Phenyl | H | OMe | N | N=CH—NH—C | | |
| I-571 | Phenyl | Phenyl | H | Cl | N | N=CH—NH—C | | |
| I-572 | Phenyl | Phenyl | H | H | N | N=CH—NH—C | | |
| I-573 | Phenyl | Phenyl | H | SMe | N | H | CH | |
| I-574 | Phenyl | Phenyl | H | CMe₃ | N | CF₃ | CH | |
| I-575 | Phenyl | Phenyl | H | OMe | N | Me | CH | |
| I-576 | Phenyl | Phenyl | H | OMe | N | H | C—NO₂ | |
| I-577 | Phenyl | Phenyl | H | OMe | C—Me | H | N | |
| I-578 | Phenyl | Phenyl | H | Me | C—Me | H | N | |

TABLE 3-continued $$\text{Structure I: Et-C(R}^4\text{)(R}^5\text{)-C(CO}_2\text{H)(R}^7\text{)-NH-pyrimidine with R}^2\text{, X, Y, R}^3\text{ substituents}$$

| No. | R⁴ | R⁵ | R⁷ | R² | X | R³ | Y | M.p. [° C.] |
|---|---|---|---|---|---|---|---|---|
| I-579 | Phenyl | Phenyl | H | OMe | CH | H | C—NO₂ | |
| I-580 | Phenyl | Phenyl | H | Me | CH | H | C—NO₂ | |
| I-581 | Phenyl | Phenyl | H | OMe | CH | H | C—NH₂ | |
| I-582 | Phenyl | Phenyl | H | OMe | C—NO₂ | OMe | CH | |
| I-583 | Phenyl | Phenyl | H | OMe | C—NO₂ | H | CH | |
| I-584 | Phenyl | Phenyl | H | Me | C—NO₂ | Me | CH | |
| I-585 | Phenyl | Phenyl | H | Me | C—NH₂ | Me | CH | |
| I-586 | Phenyl | Phenyl | H | Me | C—NO₂ | OMe | CH | |
| I-587 | Phenyl | Phenyl | H | Me | C—NH₂ | OMe | CH | |
| I-588 | Phenyl | Phenyl | Me | OMe | CH | OMe | N | |
| I-589 | Phenyl | Phenyl | Me | OMe | CH | Me | N | |
| I-590 | Phenyl | Phenyl | Me | Me | CH | Me | N | |
| I-591 | Phenyl | Phenyl | Me | OMe | N | OMe | N | |
| I-592 | 4-Methoxyphenyl | 4-Methoxyphenyl | H | OMe | CH | OMe | N | |
| I-593 | 4-Methoxyphenyl | 4-Methoxyphenyl | H | OMe | CH | Me | N | |
| I-594 | 4-Methoxyphenyl | 4-Methoxyphenyl | H | Me | CH | Me | N | |
| I-595 | 4-Methoxyphenyl | 4-Methoxyphenyl | H | Me | CH | Et | N | |
| I-596 | 4-Methoxyphenyl | 4-Methoxyphenyl | H | Et | CH | Et | N | |
| I-597 | 4-Methoxyphenyl | 4-Methoxyphenyl | H | Me | CH | CF₃ | N | |
| I-598 | 4-Methoxyphenyl | 4-Methoxyphenyl | H | OMe | CH | CF₃ | N | |
| I-599 | 4-Methoxyphenyl | 4-Methoxyphenyl | H | OMe | CH | H | N | |
| I-600 | 4-Methoxyphenyl | 4-Methoxyphenyl | H | SMe | CH | H | N | |
| I-601 | 4-Methoxyphenyl | 4-Methoxyphenyl | H | Et | CH | OMe | N | |
| I-602 | 4-Methoxyphenyl | 4-Methoxyphenyl | H | CF₃ | CH | H | N | |
| I-603 | 4-Methoxyphenyl | 4-Methoxyphenyl | H | Me | CH | H | N | |
| I-604 | 4-Methoxyphenyl | 4-Methoxyphenyl | H | Me | C—(CH₂)₃— | | N | |
| I-605 | 4-Methoxyphenyl | 4-Methoxyphenyl | H | OMe | C—(CH₂)₃— | | N | |
| I-606 | 4-Methoxyphenyl | 4-Methoxyphenyl | H | Me | C—(CH₂)₂—O | | N | |
| I-607 | 4-Methoxyphenyl | 4-Methoxyphenyl | H | OMe | C—(CH₂)₂—O | | N | |
| I-608 | 4-Methoxyphenyl | 4-Methoxyphenyl | H | OMe | N | OMe | N | |
| I-609 | 4-Methoxyphenyl | 4-Methoxyphenyl | H | NH₂ | N | NH₂ | N | |
| I-610 | 4-Methoxyphenyl | 4-Methoxyphenyl | H | NHMe | N | NHMe | N | |
| I-611 | 4-Methoxyphenyl | 4-Methoxyphenyl | H | Me | N | Me | N | |
| I-612 | 4-Methoxyphenyl | 4-Methoxyphenyl | H | SMe | N | SMe | N | |
| I-613 | 4-Methoxyphenyl | 4-Methoxyphenyl | H | H | CH | H | N | |
| I-614 | 4-Methoxyphenyl | 4-Methoxyphenyl | H | OMe | N | OMe | CH | |
| I-615 | 4-Methoxyphenyl | 4-Methoxyphenyl | H | Cl | N | Me | CH | |
| I-616 | 4-Methoxyphenyl | 4-Methoxyphenyl | H | OMe | N | N=CH—NH—C | | |
| I-617 | 4-Methoxyphenyl | 4-Methoxyphenyl | H | Cl | N | N=CH—NH—C | | |
| I-618 | 4-Methoxyphenyl | 4-Methoxyphenyl | H | H | N | N=CH—NH—C | | |
| I-619 | 4-Methoxyphenyl | 4-Methoxyphenyl | H | SMe | N | H | CH | |
| I-620 | 4-Methoxyphenyl | 4-Methoxyphenyl | H | CMe₃ | N | CF₃ | CH | |
| I-621 | 4-Methoxyphenyl | 4-Methoxyphenyl | H | OMe | N | Me | CH | |
| I-622 | 4-Methoxyphenyl | 4-Methoxyphenyl | H | OMe | N | H | C—NO₂ | |
| I-623 | 4-Methoxyphenyl | 4-Methoxyphenyl | H | OMe | C—Me | H | N | |
| I-624 | 4-Methoxyphenyl | 4-Methoxyphenyl | H | Me | C—Me | H | N | |
| I-625 | 4-Methoxyphenyl | 4-Methoxyphenyl | H | OMe | CH | H | C—NO₂ | |
| I-626 | 4-Methoxyphenyl | 4-Methoxyphenyl | H | Me | CH | H | C—NO₂ | |
| I-627 | 4-Methoxyphenyl | 4-Methoxyphenyl | H | OMe | CH | H | C—NH₂ | |
| I-628 | 4-Methoxyphenyl | 4-Methoxyphenyl | H | OMe | C—NO₂ | OMe | CH | |
| I-629 | 4-Methoxyphenyl | 4-Methoxyphenyl | H | OMe | C—NO₂ | H | CH | |
| I-630 | 4-Methoxyphenyl | 4-Methoxyphenyl | H | Me | C—NO₂ | Me | CH | |
| I-631 | 4-Methoxyphenyl | 4-Methoxyphenyl | H | Me | C—NH₂ | Me | CH | |
| I-632 | 4-Methoxyphenyl | 4-Methoxyphenyl | H | Me | C—NO₂ | OMe | CH | |
| I-633 | 4-Methoxyphenyl | 4-Methoxyphenyl | H | Me | C—NH₂ | OMe | CH | |
| I-634 | 4-Methoxyphenyl | 4-Methoxyphenyl | Me | OMe | CH | OMe | N | |
| I-635 | 4-Methoxyphenyl | 4-Methoxyphenyl | Me | OMe | CH | Me | N | |
| I-636 | 4-Methoxyphenyl | 4-Methoxyphenyl | Me | Me | CH | Me | N | |
| I-637 | 4-Methoxyphenyl | 4-Methoxyphenyl | Me | OMe | N | OMe | N | |
| I-638 | Et | Phenyl | H | OMe | CH | OMe | N | |
| I-639 | Et | Phenyl | H | Me | CH | OMe | N | |
| I-640 | Et | Phenyl | H | Me | CH | Me | N | |
| I-641 | Et | Phenyl | H | OMe | CH | OMe | CH | |
| I-642 | Et | Phenyl | H | OMe | C—Me | H | N | |
| I-643 | Et | Phenyl | H | OMe | N | H | N | |
| I-644 | Et | Phenyl | H | OMe | CH | OMe | N | |

TABLE 3-continued

Structure I: Et—C(R⁴)(R⁵)—C(CO₂H)(R⁷)—NH—[pyrimidine ring with R², X, R³, Y]

| No. | R⁴ | R⁵ | R⁷ | R² | X | R³ | Y | M.p. [° C.] |
|---|---|---|---|---|---|---|---|---|
| I-645 | Et | Phenyl | Me | OMe | N | OMe | N | |
| I-646 | Et | Phenyl | Me | Me | CH | OMe | N | |
| I-647 | Et | Phenyl | Me | Me | CH | Me | N | |

TABLE 4

Structure I: MeO—C(R⁴)(R⁵)—C(CO₂H)(R⁷)—NH—[pyrimidine ring with R², X, R³, Y]

| No. | R⁴ | R⁵ | R⁷ | R² | X | R³ | Y | M.p. [° C.] |
|---|---|---|---|---|---|---|---|---|
| I-648 | Phenyl | Phenyl | H | OMe | CH | OMe | N | |
| I-649 | Phenyl | Phenyl | H | OMe | CH | Me | N | |
| I-650 | Phenyl | Phenyl | H | Me | CH | Me | N | |
| I-651 | Phenyl | Phenyl | H | Me | CH | Et | N | |
| I-652 | Phenyl | Phenyl | H | Et | CH | Et | N | |
| I-653 | Phenyl | Phenyl | H | Me | CH | CF₃ | N | |
| I-654 | Phenyl | Phenyl | H | OMe | CH | CF₃ | N | |
| I-655 | Phenyl | Phenyl | H | OMe | CH | H | N | |
| I-656 | Phenyl | Phenyl | H | SMe | CH | H | N | |
| I-657 | Phenyl | Phenyl | H | Et | CH | OMe | N | |
| I-658 | Phenyl | Phenyl | H | CF₃ | CH | H | N | |
| I-659 | Phenyl | Phenyl | H | Me | CH | H | N | |
| I-660 | Phenyl | Phenyl | H | Me | C—(CH₂)₃— | | N | |
| I-661 | Phenyl | Phenyl | Me | OMe | C—(CH₂)₃— | | CH | |
| I-662 | Phenyl | Phenyl | Me | Me | C—(CH₂)₂—O | | N | |
| I-663 | Phenyl | Phenyl | Me | OMe | C—(CH₂)₂—O | | N | |
| I-664 | Phenyl | Phenyl | H | OMe | N | OMe | N | |
| I-665 | Phenyl | Phenyl | H | NH₂ | N | NH₂ | N | |
| I-666 | Phenyl | Phenyl | H | NHMe | N | NHMe | N | |
| I-667 | Phenyl | Phenyl | H | Me | N | Me | N | |
| I-668 | Phenyl | Phenyl | H | SMe | N | SMe | N | |
| I-669 | Phenyl | Phenyl | H | H | CH | H | CH | |
| I-670 | Phenyl | Phenyl | H | OMe | N | OMe | CH | |
| I-671 | Phenyl | Phenyl | H | Cl | N | Me | CH | |
| I-672 | Phenyl | Phenyl | H | OMe | N | N=CH—NH—C | | |
| I-673 | Phenyl | Phenyl | H | Cl | N | N=CH—NH—C | | |
| I-674 | Phenyl | Phenyl | H | H | N | N=CH—NH—C | | |
| I-675 | Phenyl | Phenyl | H | SMe | N | H | CH | |
| I-676 | Phenyl | Phenyl | H | CMe₃ | N | CF₃ | CH | |
| I-677 | Phenyl | Phenyl | H | OMe | N | Me | CH | |
| I-678 | Phenyl | Phenyl | H | OMe | N | H | C—NO₂ | |
| I-679 | Phenyl | Phenyl | H | OMe | C—Me | H | N | |
| I-680 | Phenyl | Phenyl | H | Me | C—Me | H | N | |
| I-681 | Phenyl | Phenyl | H | OMe | CH | H | C—NO₂ | |
| I-682 | Phenyl | Phenyl | H | Me | CH | H | C—NO₂ | |
| I-683 | Phenyl | Phenyl | H | OMe | CH | H | C—NH₂ | |
| I-684 | Phenyl | Phenyl | H | OMe | C—NO₂ | OMe | CH | |
| I-685 | Phenyl | Phenyl | H | OMe | C—NO₂ | H | CH | |
| I-686 | Phenyl | Phenyl | H | Me | C—NO₂ | Me | CH | |
| I-687 | Phenyl | Phenyl | H | Me | C—NH₂ | Me | CH | |
| I-688 | Phenyl | Phenyl | H | Me | C—NO₂ | OMe | CH | |
| I-689 | Phenyl | Phenyl | H | Me | C—NH₂ | OMe | CH | |
| I-690 | Phenyl | Phenyl | Me | OMe | CH | OMe | N | |
| I-691 | Phenyl | Phenyl | Me | OMe | CH | Me | N | |
| I-692 | Phenyl | Phenyl | Me | Me | CH | Me | N | |
| I-693 | Phenyl | Phenyl | Me | OMe | N | OMe | N | |

TABLE 4-continued

I

| No. | R⁴ | R⁵ | R⁷ | R² | X | R³ | Y | M.p. [° C.] |
|---|---|---|---|---|---|---|---|---|
| I-694 | Me | Phenyl | H | OMe | CH | OMe | N | |
| I-695 | Me | Phenyl | H | OMe | CH | Me | N | |
| I-696 | Me | Phenyl | H | Me | CH | Me | CH | |
| I-697 | Me | Phenyl | H | OMe | N | OMe | CH | |
| I-698 | Me | Phenyl | H | OMe | CH | H | N | |
| I-699 | Me | Phenyl | H | OMe | C—Me | H | N | |
| I-700 | Me | Phenyl | H | OMe | N | OMe | N | |
| I-701 | Me | Phenyl | Me | OMe | CH | OMe | N | |
| I-702 | Me | Phenyl | Me | OMe | N | OMe | N | |
| I-703 | Me | Phenyl | Me | Me | CH | Me | N | |
| I-704 | H | Phenyl | H | OMe | CH | OMe | N | |
| I-705 | H | Phenyl | H | OMe | CH | Me | N | |
| I-706 | H | Phenyl | H | Me | CH | Me | N | |
| I-707 | H | Phenyl | H | OMe | N | OMe | CH | |
| I-708 | H | Phenyl | H | OMe | CH | H | N | |
| I-709 | H | Phenyl | H | OMe | C—Me | H | N | |
| I-710 | H | Phenyl | H | OMe | N | OMe | N | |
| I-711 | H | Phenyl | Me | OMe | CH | OMe | N | |
| I-712 | H | Phenyl | Me | OMe | N | OMe | N | |
| I-713 | H | Phenyl | Me | Me | CH | Me | N | |

TABLE 5

I

| No. | Structure | M.p. [° C.] |
|---|---|---|
| I-714 | EtO, Ph, CO₂H, Ph, NH–pyrimidine(4,6-diOMe) | |
| I-715 | EtO, Ph, CO₂H, Ph, NH–pyrimidine(4,6-diMe) | |
| I-716 | EtO, Ph, CO₂H, Ph, NH–pyrimidine(4-OMe, 6-Me) | |
| I-717 | Ph, H, Ph, CO₂H, N(CHO)–pyrimidine(4,6-diOMe) | |
| I-718 | Ph, H, Ph, CO₂H, N(COMe)–pyrimidine(4,6-diOMe) | |
| I-719 | Ph, H, Ph, CO₂H, N(CO₂tBu)–pyrimidine(4,6-diMe) | |

TABLE 5-continued

| No. | Structure | M.p. [° C.] |
|---|---|---|
| I-720 | Ph,H-C(Ph)-CO₂H-NH-(2,4-dinitro-5-methylphenyl) | |
| I-721 | Me,H-C(4-biphenyl)-CO₂H-NH-(4,6-dimethylpyrimidin-2-yl) | |
| I-722 | Me,Me-C(4-biphenyl)-CO₂H-NH-(4,6-dimethylpyrimidin-2-yl) | |
| I-723 | Me,H-C(3-biphenyl)-CO₂H-NH-(4,6-dimethylpyrimidin-2-yl) | |
| I-724 | H,H-C(3-biphenyl)-CO₂H-NH-(4,6-dimethylpyrimidin-2-yl) | |
| I-725 | Me,Me-C(3-biphenyl)-CO₂H-NH-(4,6-dimethylpyrimidin-2-yl) | |
| I-726 | Ph,H-C(Ph)-CO₂H-NH-(4-hydroxy-6-methylpyrimidin-2-yl) | |
| I-727 | Ph,H-C(Ph)-CO₂H-NH-(4,6-dihydroxypyrimidin-2-yl) | |
| I-728 | Ph,H-C(Ph)-CO₂H-NH-(5-cyano-4-methylpyrimidin-2-yl) | |
| I-729 | Ph,H-C(Ph)-CO₂H-NH-(5-cyano-4-methylpyrimidin-2-yl) | |

TABLE 5-continued

| No. | Structure | M.p. [° C.] |
|---|---|---|
| I-730 | 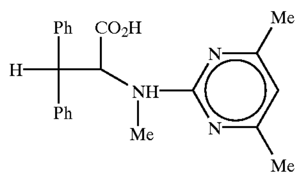 | |
| I-731 | 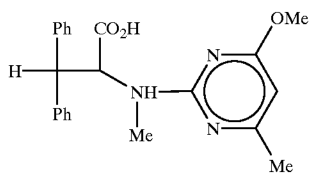 | |
| I-732 | 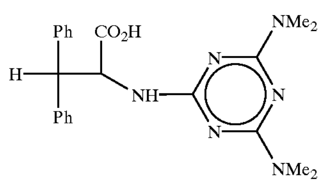 | |
| I-733 | 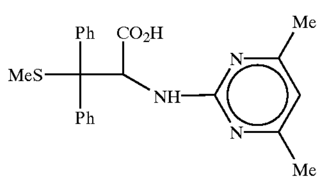 | |
| I-734 | 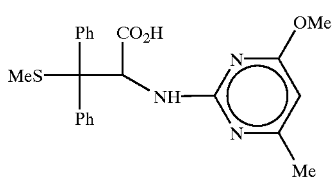 | |
| I-735 | 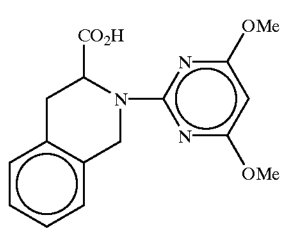 | |
| I-736 | 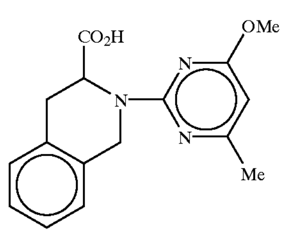 | |
| I-737 | | |
| I-738 | | |
| I-739 | | |
| I-740 | | |
| I-741 | | |

TABLE 5-continued

![Structure I with R4, R5, CO2H, NH, pyrimidine ring with R2, R3, X, Y and MeO group]

I

| No. | Structure | M.p. [° C.] |
|-----|-----------|-------------|
| I-742 | 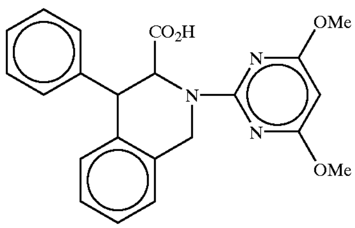 | |
| I-743 | 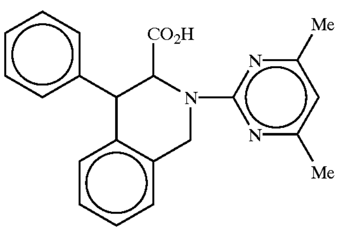 | |
| I-744 | 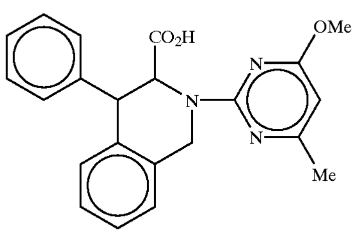 | |
| I-745 | 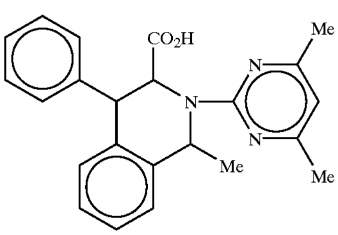 | |
| I-746 | 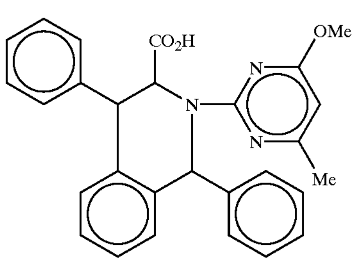 | |
| I-747 | | |
| I-748 | | |
| I-749 | | |
| I-750 | | |
| I-751 | | |

TABLE 5-continued

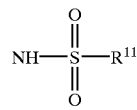

| No. | Structure | M.p. [° C.] |
|---|---|---|
| I-752 | 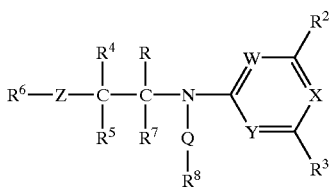 | |
| I-753 | 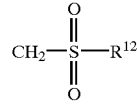 | |

We claim:
1. A compound of formula I

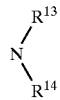

where R is tetrazolyl, cyano or a radical

where $R^1$ has the following meanings:
b) succinimidyl;
d) a radical

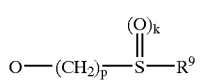

where k is 0, 1 or 2, p is 1, 2, 3 or 4, and $R^9$ is $C_1$–$C_4$-alkyl, $C_3$–$C_7$-cycloalkyl, $C_3$–$C_6$-alkenyl, $C_3$–$C_6$-alkynyl or phenyl which is unsubstituted or substituted by one or more of the following radicals: halogen, nitro, cyano, $C_1$–$C_4$-alkyl, $C_1$–$C_4$-haloalkyl, hydroxyl, $C_1$–$C_4$-alkoxy, $C_1$–$C_4$-alkylthio, mercapto, amino, $C_1$–$C_4$-alkylamino and $C_1$–$C_4$-dialkylamino;

e) a radical $OR^{10}$, where $R^{10}$ is: hydrogen, an alkali metal cation or an alkaline earth metal cation, ammonium or a physiologically tolerated alkylammonium ion, $C_3$–$C_8$-cycloalkyl; $C_1$–$C_8$-alkyl; benzyl which is unsubstituted or substituted by one or more of the following radicals: halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino and $C_1$–$C_4$-dialkylamino; $C_3$–$C_6$-alkenyl or $C_3$–$C_6$-alkynyl, which is unsubstituted or carries one to five halogen atoms; phenyl which is unsubstituted or substituted by one to five halogen atoms and/or from one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino and $C_1$–$C_4$-dialkylamino;

f) a radical $$\text{NH}-\overset{\overset{\displaystyle O}{\|}}{\underset{\underset{\displaystyle O}{\|}}{S}}-R^{11}$$

where $R^{11}$ is: $C_1$–$C_4$-alkyl, $C_3$–$C_6$-alkenyl, $C_3$–$C_6$-alkynyl, $C_3$–$C_8$-cycloalkyl, which radicals are unsubstituted or carry a $C_1$–$C_4$-alkoxy, $C_1$–$C_4$-alkylthio and/or phenyl radical; phenyl which is unsubstituted or substituted by one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino and $C_1$–$C_4$-dialkylamino;

g) a radical $$\text{CH}_2-\overset{\overset{\displaystyle O}{\|}}{\underset{\underset{\displaystyle O}{\|}}{S}}-R^{12}$$

where $R^{12}$ is $C_1$–$C_4$-alkyl, $C_3$–$C_6$-alkenyl, $C_3$–$C_6$-alkynyl, $C_3$–$C_8$-cycloalkyl, which radicals are unsubstituted or carry a $C_1$–$C_4$-alkoxy, $C_1$–$C_4$-alkylthio and/or phenyl radical; phenyl which is unsubstituted or substituted by one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino and $C_1$–$C_4$-dialkylamino;

h) a radical $$\text{N}\overset{\displaystyle R^{13}}{\underset{\displaystyle R^{14}}{\diagdown}}$$

where $R^{13}$ and $R^{14}$, independently of one another, are hydrogen, $C_1$–$C_7$-alkyl, $C_3$–$C_7$-cycloalkyl, $C_3$–$C_7$-alkenyl, $C_3$–$C_7$-alkynyl, benzyl or phenyl which are unsubstituted or substituted by one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino and $C_1$–$C_4$-dialkylamino; or $R^{13}$ and $R^{14}$ together form a $C_4$–$C_7$-alkylene chain or a chain consisting of 4 to 7 methylene members and one member selected from the group of oxygen, nitrogen and sulfur, which chain is unsubstituted or substituted by $C_1$–$C_4$-alkyl; tetrazole or nitrile; and W is nitrogen;

$R^2$ is hydrogen, halogen, $C_1$–$C_4$-alkyl, $C_1$–$C_4$-haloalkyl, $C_1$–$C_4$-alkoxy, $C_1$–$C_4$-haloalkoxy, hydroxyl, mercapto, $C_1$–$C_4$-alkylthio, nitro, amino, $C_1$–$C_4$-alkylamino or $C_1$–$C_4$-dialkylamino, cyano, phenyl which is unsubstituted or carries one to three of the following: halogen, hydroxyl, amino, mono-($C_1$–$C_3$)-amino, dialkyl-($C_1$–$C_3$)-amino, $C_1$–$C_3$-alkyl, $C_1$–$C_3$-alkoxy, mercapto and $C_1$–$C_3$-alkylthio; or X is $CR^{15}$ where $R^{15}$ is hydrogen or $C_1$–$C_5$-alkyl, $C_1$–$C_5$-alkoxy, $C_1$–$C_5$-alkylthio, nitro, phenyl, hydroxyl, mercapto, halogen, amino, $C_1$–$C_4$-alkylamino, $C_1$–$C_4$-dialkylamino or cyano, or $R^{15}$ and $R^2$ to form a 5- to 6-membered alkylene or alkylidene ring or a 5- or 6-membered alkylene or alkenylene ring wherein one or two carbon ring members are replaced by a nitrogen, sulfur or oxygen atom, and which ring is unsubstituted or carries one to three of the following radicals: halogen, nitro, cyano, hydroxyl, mercapto, $C_1$–$C_3$-alkyl, $C_1$–$C_3$-haloalkyl, $C_1$–$C_3$-alkoxy, $C_1$–$C_3$-alkylthio, amino, $C_1$–$C_3$-alkylamino and $C_1$–$C_3$-dialkylamino; or $R^{15}$ and $R^3$ together with the adjacent carbon atom form a 5- or 6-membered alkylene or alkylidene ring or a 5- or 6-membered alkylene or alkenylene ring wherein one or two carbon ring members are replaced by a nitrogen, sulfur or oxygen atom, and which ring is unsubstituted or carries one to three of the following radicals: halogen, nitro, cyano, hydroxyl, mercapto, $C_1$–$C_3$-alkyl, $C_1$–$C_3$-haloalkyl, $C_1$–$C_3$-alkoxy, $C_1$–$C_3$-alkylthio, amino, $C_1$–$C_3$-alkylamino and $C_1$–$C_3$-dialkylamino;

$R^3$ is one of the radicals given for $R^2$,

Y is nitrogen;

$R^4$ is phenyl which is unsubstituted or carries one or more of the following radicals halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, phenyl, $C_1$–$C_4$-alkylthio, amino, $C_1$–$C_4$-alkylamino and $C_1$–$C_4$-dialkylamino, or $R^4$ and $R^5$ are each phenyl groups which are connected to each other in the ortho positions by a direct linkage, a methylene, ethylene or ethenylene group, an oxygen or sulfur atom or an $SO_2$, NH or N-alkyl group;

$R^5$ is cyclohexyl, phenyl or naphthyl which is unsubstituted or carries from one to three of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, phenyl, $C_1$–$C_4$-alkylthio, amino, $C_1$–$C_4$-alkylamino, $C_1$–$C_4$-dialkylamino and two radicals on adjacent carbon atoms which form an alkylene or alkylidene group, a ring having 5 or 6 ring members selected from methylene, methylidene and oxygen;

$R^6$ is hydrogen, $C_1$–$C_4$-alkyl or $C_1$–$C_4$-haloalkyl

Z is a single bond, oxygen, sulfur, sulfinyl or sulfonyl;

$R^7$ is hydrogen or $C_1$–$C_4$-alkyl, $C_2$–$C_4$-alkenyl, $C_2$–$C_4$-alkynyl;

Q is a single bond, a

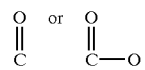

group $R^8$ is hydrogen, $C_1$–$C_4$-alkyl, $C_2$–$C_4$-alkenyl, phenyl or benzyl, and $R^8$ can furthermore be directly connected to $R^5$ as described above, in which case $R^8$ is a CH—$R^{17}$ group where $R^{17}$ is hydrogen, $C_1$–$C_4$-alkyl, phenyl or phenyl which is mono- to trisubstituted by methoxy, or is one of the following radicals

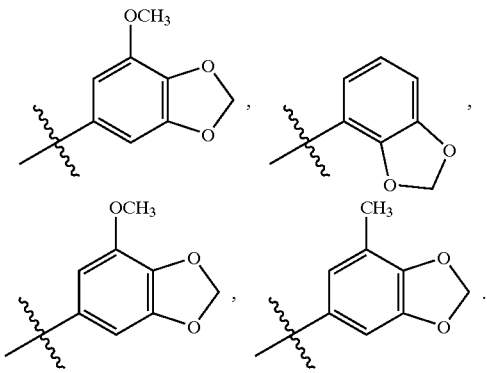

2. A method of treating hypertension in a patient in need of such treatment, which comprises administering an effective amount of the compound I defined in claim 1 to said patient.

3. The method defined in claim 2, wherein the amount of the compound I is adapted to be effective to antagonize endothelin.

4. A pharmaceutical composition comprising an effective amount of the compound I defined in claim 1 and at least one conventional pharmaceutical aid.

5. The compound I defined in claim 1 wherein $R^2$ is hydrogen, halogen, $C_1$–$C_4$-alkyl, $C_1$–$C_4$-haloalkyl, nitro, $C_1$–$C_4$-alkoxy, $C_1$–$C_4$-alkylthio, cyano, amino, methylamino, hydroxyl or dimethylamino.

6. The compound I defined in claim 1 wherein X is $CR^{15}$ and $R^{15}$ is hydrogen or $C_1$–$C_4$-alkyl, $C_1$–$C_4$-alkoxy, nitro, cyano, halogen or phenyl.

7. The compound I defined in claim 1 wherein $R^3$ is hydrogen, halogen, $C_1$–$C_4$-alkyl, $C_1$–$C_4$-haloalkyl, nitro, $C_1$–$C_4$-alkoxy, $C_1$–$C_4$-alkylthio, cyano, amino, methylamino, hydroxyl or dimethylamino.

8. The compound I defined in claim 1 wherein $R^4$ is phenyl which is unsubstituted or carries one or more of the following radicals: halogen, $C_1$–$C_4$-alkyl, $C_1$–$C_4$-alkoxy and phenyl, or $R^4$ and $R^5$ are each phenyl groups which are connected to each other in the ortho positions by a direct linkage, a methylene or ethylene group, or an oxygen atom.

9. The compound I defined in claim 1 wherein $R^5$ is phenyl which is unsubstituted or carries one or more of the following radicals: halogen, $C_1$–$C_4$-alkyl, $C_1$–$C_4$-alkoxy, phenyl and, bonded to two adjacent carbon ring members of the phenyl ring, 1,3-dioxomethylene and 1,4-dioxoethylene.

10. The compound I defined in claim 1 wherein $R^6$ is hydrogen or $C_1$–$C_4$-alkyl.

11. The compound I defined in claim 1 wherein Z is a single bond, oxygen or sulfur.

12. The compound I defined in claim 1 wherein $R^7$ is hydrogen or $C_1$–$C_4$-alkyl.

13. The compound I defined in claim 1 wherein $R^8$ is hydrogen or $C_1$–$C_4$-alkyl.

14. The compound I defined in claim 1 wherein $R^2$ is hydrogen, chlorine, methyl, ethyl, trifluoromethyl, nitro, methoxy, ethoxy, hydroxyl, methylthio, amino, methylamino or dimethylamino.

15. The compound I defined in claim 1 wherein X is $CR^{15}$ and $R^{15}$ is hydrogen, methyl, nitro or cyano.

16. The compound I defined in claim 1 wherein $R^3$ is hydrogen, chlorine, methyl, ethyl, trifluoromethyl, nitro, methoxy, ethoxy, hydroxyl, methylthio, amino, methylamino or dimethylamino.

17. The compound I defined in claim 1 wherein $R^4$ is phenyl which is unsubstituted or carries one or two methoxy groups, or $R^4$ and $R^5$ are each phenyl groups which are connected to each other in the ortho positions by a direct linkage, a methylene or ethylene group.

18. The compound I defined in claim 1 wherein $R^5$ is phenyl which is unsubstituted or carries one or two of the following: methoxy, 1,3-dioxomethylene or 1,4-dioxoethylene, or $R^5$ is phenyl which is unsubstituted or carries one or two of the following: methoxy, 1,3-dioxomethylene or 1,4-dioxoethylene, which phenyl ring is bonded in the ortho position to $R^8$ to form a 6-membered ring wherein Q denotes a direct bond and $R^8$ denotes $CHR^{17}$.

19. The compound I defined in claim 1 wherein $R^6$ is hydrogen, methyl, ethyl, n-propyl or 1-methylethyl.

20. The compound I defined in claim 1 wherein $R^7$ is hydrogen or methyl.

21. The compound I defined in claim 1 wherein $R^8$ is hydrogen, methyl or 1,1-dimethylethyl.

22. The compound I defined in claim 1 wherein $R^5$ is one of the following radicals

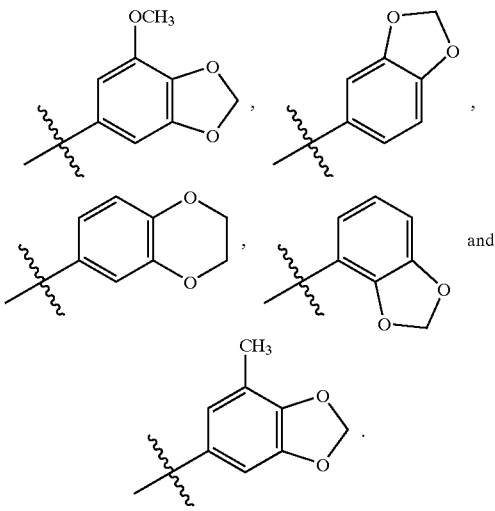

23. The compound I defined in claim 1 wherein $R^{15}$ is hydrogen.

* * * * *